United States Patent
Nomura et al.

(10) Patent No.: US 6,812,436 B2
(45) Date of Patent: Nov. 2, 2004

(54) TEMPERATURE CONTROL APPARATUS FOR EXHAUST GAS SENSOR

(75) Inventors: Masahiko Nomura, Tokyo (JP); Kohji Hashimoto, Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 31 days.

(21) Appl. No.: 10/376,595

(22) Filed: Mar. 3, 2003

(65) Prior Publication Data

US 2004/0047396 A1 Mar. 11, 2004

(30) Foreign Application Priority Data

Sep. 6, 2002 (JP) ..................................... 2002-261257

(51) Int. Cl.[7] ............................................. H05B 1/02
(52) U.S. Cl. .................... 219/497; 219/202; 219/505; 219/481; 219/492; 219/508; 219/697; 219/703
(58) Field of Search ................................ 219/494, 492, 219/497, 499, 501, 505, 481, 202, 205, 508; 123/697; 307/117, 39–41

(56) References Cited

U.S. PATENT DOCUMENTS

| | | | | |
|---|---|---|---|---|
| 4,109,615 A | * | 8/1978 | Asano | 123/686 |
| 4,348,583 A | * | 9/1982 | Bube et al. | 219/497 |
| 4,524,264 A | * | 6/1985 | Takeuchi et al. | 219/497 |
| 5,696,313 A | * | 12/1997 | Hafele | 73/23.31 |
| 6,476,364 B1 | * | 11/2002 | Shimamura et al. | 219/494 |

FOREIGN PATENT DOCUMENTS

| | | | | |
|---|---|---|---|---|
| JP | 07069037 A | * | 3/1995 | ............ B60H/1/00 |
| JP | 2001-041923 | | 2/2001 | |
| JP | 2001-073827 | | 3/2001 | |
| JP | 2002-021631 | | 1/2002 | |
| JP | 2002-048763 | | 2/2002 | |

* cited by examiner

Primary Examiner—Mark Paschall
(74) Attorney, Agent, or Firm—Sughrue Mion, PLLC

(57) ABSTRACT

A temperature control apparatus for an exhaust gas sensor can promptly heat the exhaust gas sensor with an electric heater up to an activation temperature while preventing thermal shock damage thereof due to water immediately after engine starting. Energization of an electric heater arranged near an exhaust gas sensor is controlled by a CPU cooperating with a ROM through a switching element. A low voltage is supplied for evaporation of the water by a first preheater immediately after engine starting, and enhanced preheating is subsequently carried out by a second preheater for preventing thermal shock on the exhaust gas sensor. Thereafter, a heating controller performs automatic control with a proper activation temperature of the exhaust gas sensor being made as a target. The temperature controlled by the first preheater is set to such a temperature level at which rapid cooling damage of the exhaust gas sensor due to the water will not be caused but the water can be evaporated.

17 Claims, 7 Drawing Sheets

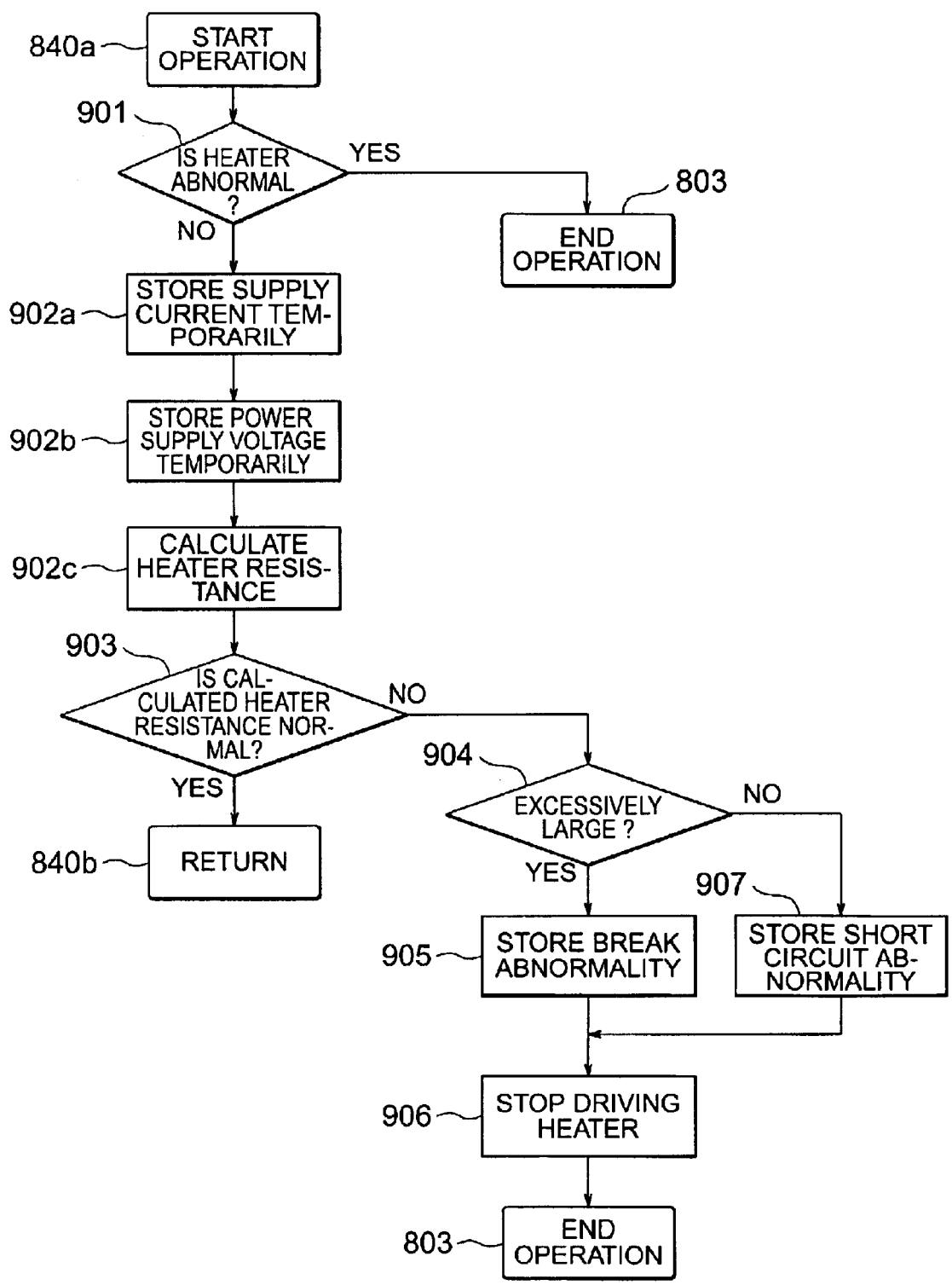

TEMPERATURE CONTROL APPARATUS FOR EXHAUST GAS SENSOR

BACKGROUND OF THE INVENTION

1. Field of the Invention

The present invention relates to a temperature control apparatus for an exhaust gas sensor capable of detecting the concentration of a specific component in the exhaust gas of an internal combustion engine, and more particularly, it relates to such a temperature control apparatus for an exhaust gas sensor which is adapted to be used with a device having an electric heater arranged in the vicinity of the exhaust gas sensor to activate it at an early stage immediately after the starting of an internal combustion engine, and which is able to heat the exhaust gas sensor so as to promptly raise its temperature to an activation temperature thereof while preventing rapid cooling damage or rapid heating damage (thermal shock damage) of the exhaust gas sensor and/or the electric heater resulting from the splashing or spattering of the condensed moisture (pour water) contained in the exhaust gas during cold starting of the engine.

2. Description of the Related Art

In general, there has been well known the technique that the oxygen concentration in the exhaust gas of an internal combustion engine is detected to control the air fuel ratio (i.e., ratio of air to fuel) of a mixture supplied to the internal combustion engine in a feedback manner, thereby purifying the exhaust gas and improving fuel consumption.

At this case, in order to accurately perform feedback control on the air fuel ratio, it is necessary to keep the temperature of an exhaust gas sensor in an activation range thereof (about 800° C.) to stabilize the detection characteristic of oxygen concentration.

Accordingly, in the past, a temperature control apparatus for an exhaust gas sensor has been proposed in which the energization of a ceramic heater built into the exhaust gas sensor is controlled to keep the temperature of the exhaust gas sensor at a constant level (about 800° C.).

In addition, it is desirable to rapidly heat the exhaust gas sensor to a proper activation temperature upon starting of the internal combustion engine.

A method for detecting of the temperature of an exhaust gas sensor as a basic technology of such a kind of control apparatus can be seen in, for instance, Japanese patent application laid-open No. 2002-21631 (first prior art document) entitled "Heater Control Apparatus for the Exhaust Gas Sensor".

In the apparatus described in this publication, there are used a method of detecting the internal resistance value of an exhaust gas sensor and estimating the temperature of the exhaust gas sensor itself based on the internal resistance value thereof thus detected, and another method of detecting the ambient temperature of an exhaust gas sensor by measuring the resistance value of a heater built in the exhaust gas sensor.

In addition, Japanese patent application laid-open No. 2002-48763 (second prior art document) entitled "Heater Control Apparatus for Gas Concentration Sensor" discloses a method of performing preheating control on a heater according to a reduced voltage during starting of an internal combustion engine so as to avoid rapid heating of the heater at the time of cold starting, thereby preventing damage to elements of the heater due to thermal shock during rapid heating.

Moreover, Japanese patent application laid-open No. 2001-73827 (third prior art document) entitled "Exhaust Gas Sensor and Control Apparatus therefor" discloses a method of using a double structure protector, a protector heater and a sensor heater in combination so as to prevent damage to elements of the heater due to rapid cooling thermal shock resulting from the splashing or spattering of condensed water at the time of cold starting.

Furthermore, Japanese patent application laid-open No. 2001-41923 (fourth prior art document) entitled "Oxygen Concentration Detection Apparatus" discloses a means for determining the presence or absence of condensed water and a control means for limiting power supply to a heater in order to prevent damage to elements of the heater due to rapid cooling thermal shock resulting from the splashing or spattering of condensed water at the cold starting of an internal combustion engine.

However, in the above-mentioned first and second prior art documents, there is no mention about pour water rapid cooling thermal shock resulting from the splashing or spattering of condensed water at cold starting, and hence it is impossible to avoid damage to elements of the heater during cold starting.

Further, in the above-mentioned third and fourth prior art documents, no discussion is made about thermal shock due to rapid heating of the heater upon engine starting, and hence it is also impossible to avoid heater element damage due to rapid heating.

Since activating an exhaust gas sensor at an early stage during starting of an internal combustion engine is liable to cause damage to the exhaust gas sensor itself and an electric heater due to thermal shock, as is well-known, it is extremely difficult to achieve the early activation of the exhaust gas sensor as well as the prevention of damage to elements of these sensor and heater (i.e., these are objects giving rise to mutually conflicting problems).

For instance, in the third prior art document, two kinds of heater control are required and hence the apparatus as a whole is complicated in structure, thus leading to an increase in costs.

With the conventional exhaust gas sensor temperature control apparatuses, a variety of improvements have been proposed as referred to above, but they still have a common problem that it is impossible to totally improve the prevention of damage to an exhaust gas sensor and an electric heater as well as the early activation of the exhaust gas sensor.

SUMMARY OF THE INVENTION

The present invention is intended to obviate the problems as referred to above, and has for its primary object to provide a temperature control apparatus for an exhaust gas sensor which is equipped with a control means for an electric heater capable of promptly attaining an activation temperature thereof while preventing rapid cooling and rapid heating damage to the exhaust gas sensor and the electric heater.

Another object of the present invention is to provide a temperature control apparatus for an exhaust gas sensor which is equipped with a control means for an electric heater required to prevent the stain or fouling deterioration of the exhaust gas sensor even when it becomes impossible to detect exhaust gas owing to a short circuit, an open circuit, or a break of wiring or the like despite the fact that the exhaust gas sensor itself is operating in a normal state.

Bearing the above objects in mind, according to one aspect, the present invention resides in a temperature control apparatus for an exhaust gas sensor which is mounted on an exhaust pipe of an internal combustion engine for detecting the concentration of a specific component in an exhaust gas therein. The apparatus includes: an electric heater for heating the exhaust gas sensor; a switching element connected in series to the electric heater for turning on and off the supply of electric power to the electric heater; and a temperature control part for performing on/off control on the switching element so as to maintain the temperature of the exhaust gas sensor at a predetermined value. The temperature control part includes: a heating control part for performing heating control on the exhaust gas sensor in accordance with the temperature of the exhaust gas sensor; and a first preheater part and a second preheater for preheating the exhaust gas sensor upon starting of the internal combustion engine. The heating control part includes: a resistance value measurement part for measuring a resistance value of the exhaust gas sensor or a resistance value of the electric heater; a temperature determination part for determining based on the resistance value of the exhaust gas sensor or the resistance value of the electric heater whether the temperature of the exhaust gas sensor is in the vicinity of a proper activation temperature thereof; and a feedback control part for controlling the on/off state of the switching element in accordance with a correlation characteristic of a target temperature and the resistance value of the exhaust gas sensor or the resistance value of the electric heater with the proper activation temperature of the exhaust gas sensor being made as the target temperature. The first preheating part includes a first energization control part for applying a first voltage to the electric heater in a first period. The second preheating part includes a second energization control part for applying a second voltage higher than the first voltage to the electric heater in a second period following the first period. The first and second preheating parts operate prior to the operation of the feedback control part.

According to another aspect, the present invention resides in a temperature control apparatus for an exhaust gas sensor which is mounted on an exhaust pipe of an internal combustion engine for detecting the concentration of a specific component in an exhaust gas therein. The apparatus includes: an electric heater for heating the exhaust gas sensor; a switching element connected in series to the electric heater for turning on and off the supply of electric power to the electric heater; and a temperature control part for performing on/off control on the switching element so as to maintain the temperature of the exhaust gas sensor at a predetermined value. The temperature control part includes; a heating control part for performing heating control on the exhaust gas sensor in accordance with the temperature of the exhaust gas sensor; and a preheating part for preheating the exhaust gas sensor upon starting of the internal combustion engine. The heating control part includes: a resistance value measurement part for measuring a resistance value of the exhaust gas sensor or a resistance value of the electric heater; a temperature determination part for determining based on the resistance value of the exhaust gas sensor or the resistance value of the electric heater whether the temperature of the exhaust gas sensor is in the vicinity of a proper activation temperature thereof; and a feedback control part for controlling the on/off state of the switching element in accordance with a correlation characteristic of a target temperature and the resistance value of the exhaust gas sensor or the resistance value of the electric heater with the proper activation temperature of the exhaust gas sensor being made as the target temperature. The preheating part includes a first energization control part for applying a preheating voltage to the electric heater in a prescribed period, and operates prior to the operation of the feedback control part. The heating control part includes: a sensor line abnormality detection part for detecting an abnormality of the exhaust gas sensor; and a heating keeping part for keeping heating the exhaust gas sensor in response to the sensor line abnormality detection part. The sensor line abnormality detection part generates a sensor line abnormality determination signal upon detection of an open-circuit state or a short-circuit state of a signal line for the exhaust gas sensor. The heating keeping part includes a second energization control part for continuously applying a keeping voltage higher than the preheating voltage to the electric heater upon generation of the sensor line abnormality determination signal.

The above and other objects, features and advantages of the present invention will become more readily apparent to those skilled in the art from the following detailed description of preferred embodiments of the present invention taken in conjunction with the accompanying drawings.

BRIEF DESCRIPTION OF THE DRAWINGS

FIG. 9 is a flow chart explaining in detail heater resistance value calculation processing (step 840) in FIG. 8.

DESCRIPTION OF THE PREFERRED EMBODIMENTS

Figure 1:
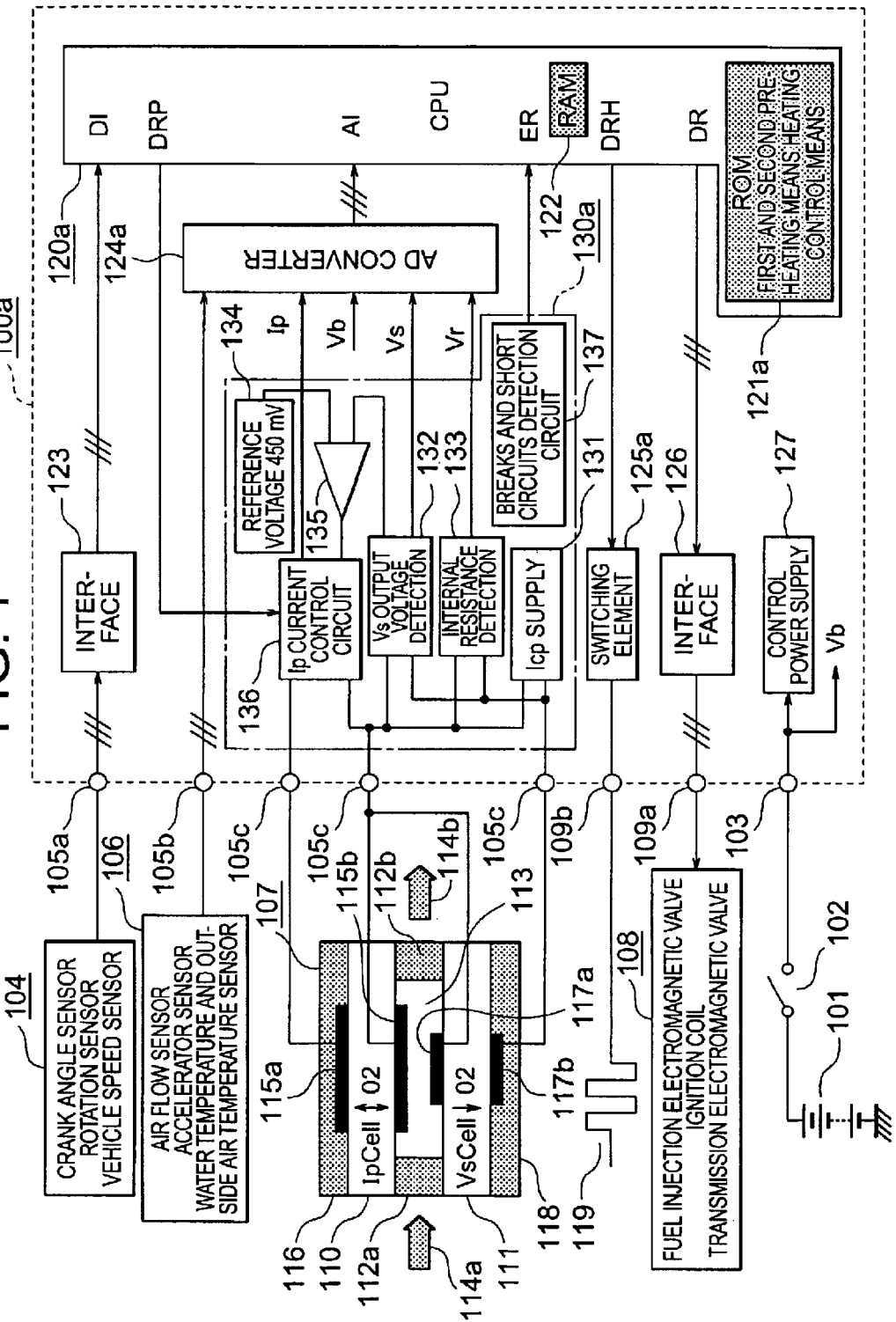
FIG. 1 is a block diagram showing a temperature control apparatus for an exhaust gas sensor according to a first embodiment of the present invention.
Figure 2:
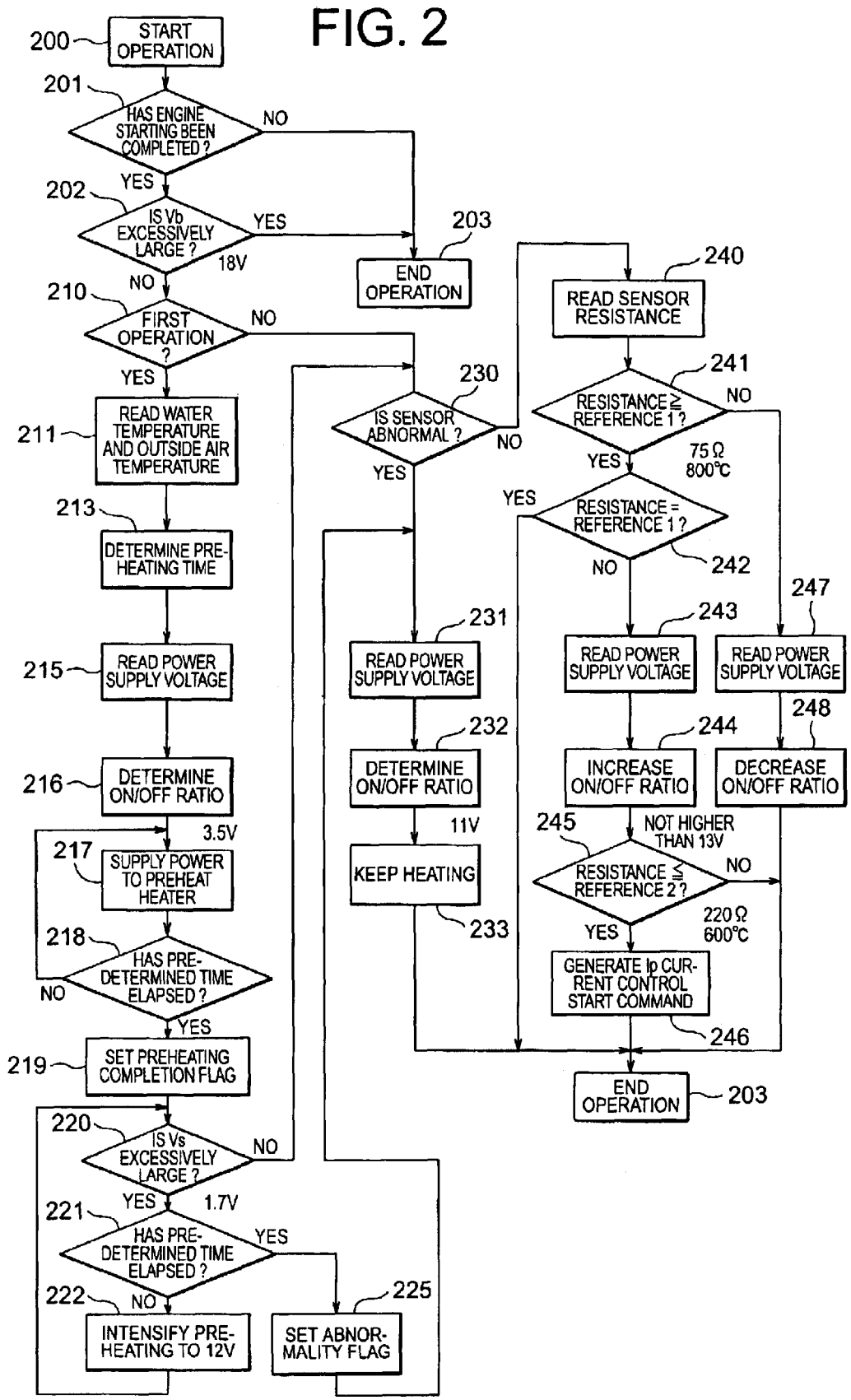
FIG. 2 is a flow chart illustrating the operation of the temperature control apparatus for an exhaust gas sensor according to the first embodiment of the present invention.

Hereinafter, preferred embodiments of the present invention will be described in detail while referring to the accompanying drawings.
Embodiment 1.
FIG. 1 is a block diagram showing a temperature control apparatus for an exhaust gas sensor according to a first embodiment of the present invention, and FIG. 2 is a flow chart illustrating the operation of the temperature control apparatus for an exhaust gas sensor according to the first embodiment of the present invention. FIG. 3 through FIG. 6 are explanatory views illustrating the operation of the temperature control apparatus for an exhaust gas sensor according to the first embodiment of the present invention.

In FIG. 1, the temperature control apparatus, generally designated at reference numeral 10a, has the function of a fuel injection control device for a vehicular internal combustion engine, and is supplied with electric power from a vehicle-mounted battery 101 of 12 volts (hereinafter simply referred to as a "battery") for example through a power supply switch 102 and a power supply terminal 103.

A sensor switch group 104 includes a variety of well-known sensors such as a crank angle sensor for detecting the rotational angle or position of an engine crankshaft, a rotation sensor for detecting the rotational speed (or number of rotations per minute) of the internal combustion engine, a vehicle speed sensor for detecting the speed of a vehicle, etc., and generates corresponding digital on/off signals. The sensor switch group 104 has output terminals connected to a control terminal group 105a of the temperature control apparatus 100a.

An analog sensor group 106 comprises a variety of sensors which include, for example, an air flow sensor, an accelerator sensor, a water temperature sensor, an ambient or outside air temperature sensor, etc., and which respectively generate voltage signals corresponding to the detected levels thereof. The analog sensor group 106 has output terminals connected to a control terminal group 105b of the temperature control apparatus 100a.

An exhaust gas sensor, generally designated at reference numeral 107, is arranged in an exhaust pipe (not shown) of the internal combustion engine for detecting the concentration of a specific component of the exhaust gas discharged from the internal combustion engine. The exhaust gas sensor 107 has output terminals connected to a control terminal group 105c of the temperature control apparatus 100a.

An electric load group 108 includes actuators for a fuel injection electromagnetic valve, an ignition coil, a transmission electromagnetic valve, etc., and has output terminals connected to an output terminal group 109a of the temperature control apparatus 100a.

An electric heater 119 is connected to an output terminal 109b of the temperature control apparatus 100a.

The exhaust gas sensor 107 includes the following components 110 through 118.

An oxygen pump element (IpCell) 110 and an oxygen concentration cell element (VsCell) 111 are each made of a zirconia solid electrolyte material.

The oxygen pump element 110 pumps out from or supplies to a gas detection chamber 113 (to be described later) an amount of oxygen corresponding to the polarity (positive or negative) and magnitude of the pump current Ip supplied thereto from a pump current control circuit 136 (to be described later).

In addition, the oxygen concentration cell element 111 generates, based on an oxygen concentration reference generation electric current Icp supplied from an oxygen concentration reference generation current supply circuit 131 (to be described later), a voltage Vs across battery cell element terminals (hereinafter referred to as a battery cell element interterminal voltage Vs), which corresponds to the concentration of oxygen on a gas detection chamber 113 side with the oxygen concentration on a battery cell element electrode 117b (to be described later) side being made as an oxygen concentration reference.

A pair of gas passageway walls 112a, 112b are made of a gas diffusion porous material and are arranged between the oxygen pump element 110 and the oxygen concentration cell element 111.

The gas detection chamber 113 is defined by the oxygen pump element 110, the oxygen concentration cell element 111 and the pair of gas passageway walls 112a, 112b.

Arrows 114a, 114b indicate the direction in which the exhaust gas passes through the gas detection chamber 113.

As shown by the arrows 114a, 114b, part of the exhaust gas flow is introduced from the gas passageway wall 112a into the gas detection chamber 113 and is discharged to the outside of the exhaust gas sensor 107 through the gas passageway wall 112b.

A pair of pump element electrodes 115a, 115b are arranged on opposed surfaces of the oxygen pump element 110 in an opposed relation with respect to each other.

A protective layer 116 covers the pump element electrode 115a.

A pair of battery cell element electrodes 117a, 117b are also arranged on the opposed surfaces of the oxygen concentration cell element 111 in an opposed relation with respect to each other.

A protective layer 118 covers the battery cell element electrode 117b.

The electrodes 115a, 117b, 115b and 117a are respectively connected to the control terminal group 105c of the temperature control apparatus 100a.

The battery cell element electrodes 117a, 117b of the oxygen concentration cell element 111 are connected to the oxygen concentration reference generation current supply circuit 131 in the temperature control apparatus 100a so that they generates the battery cell element interterminal voltage Vs, which corresponds to the oxygen concentration on the gas detection chamber 113 side with the battery cell element electrode 117b being made as an oxygen concentration reference, based on the oxygen concentration reference generation electric current Icp supplied from the oxygen concentration reference generation current supply circuit 131.

Moreover, the pump element electrodes 115a, 115b of the oxygen pump element 110 are connected to the pump current control circuit 136 in the temperature control apparatus 100a so that the oxygen pump element 110 pumps out from or supplies to the gas detection chamber 113 an amount of oxygen corresponding to the polarity (positive or negative) and magnitude of the pump current Ip supplied from the pump current control circuit 136.

As a result, the oxygen in the gas detection chamber 113 is discharged therefrom or supplied thereto so that the oxygen concentration of the gas detection chamber 113 can be controlled to be a specified value.

Therefore, the exhaust gas sensor 107 functions as a linear sensor that can measure the oxygen concentration of the gas detection chamber 113 by detecting the pump current.

The electric heater 119 is constructed integrally with the exhaust gas sensor 107, and is made of ceramics with its one end being connected to a corresponding output terminal 109b of the temperature control apparatus 100a. Also, though not illustrated here, the other end of the electric heater 119 is connected with the battery 101 through the power supply switch 102.

The temperature control apparatus 10a includes the following components 120a through 127 and 130a through 137.

Specifically, a CPU 120a functions as a microprocessor including a ROM 121a as a nonvolatile program memory (e.g., flash memory, etc.) and a RAM 122 as an arithmetic calculation memory, and it cooperates with the ROM 121a and the RAM 122.

The ROM (program memory) 121a cooperates with the CPU 120a and the RAM 122 to function as a temperature control means for controlling a switching element 125a in an on/off manner so as to maintain the temperature of the exhaust gas sensor 107 at a predetermined value.

The temperature control means includes a heating control means for performing heating control on the exhaust gas sensor 107 in accordance with the temperature thereof, and a first preheating means and a second preheating means for preheating the exhaust gas sensor 107 at the time of starting of the internal combustion engine.

Further, the temperature control means constituted by the CPU 120a includes a resistance value measurement means for measuring the resistance value of the exhaust gas sensor 107 or of the electric heater 119, and a temperature determination means for determining, based on the resistance value detected by the resistance value measurement means, whether the exhaust gas sensor 107 is in the vicinity of a proper activation temperature.

The temperature control means further includes a feedback control means for controlling the on/off state of the switching element 125a in accordance with the correlation characteristic of a target temperature and the resistance value detected by the resistance value measurement means, with the proper activation temperature of the exhaust gas sensor 107 being made as the target temperature.

The first preheating means includes a first energization control means for applying a first voltage to the electric heater 119 in a first period, and the second preheating means includes a second energization control means for applying a second voltage higher than the first voltage to the electric heater 119 in a second period subsequent to the first period. The first and second preheating means operate prior to the operation or actuation of the feedback control means.

An interface 123 constitutes an input circuit of the CPU 120a, and has a voltage level conversion function, a noise filtering function, and a data selection function for signals input thereto. The input signals from the sensor switch group 104 are input to a DI port (input terminal for the sensor switch group) of the CPU 120a through the interface 123.

A multichannel A/D converter 124a converts analog input signals from the analog sensor group 106 into corresponding digital signals, which are then input to an AI port (input terminal for the analog input signal group) of the CPU 120a.

The switching element 125a comprises a power transistor connected to a DRH port (output terminal for a heater drive signal) of the CPU 120a. The switching element 125a is driven by a control signal of a variable on/off ratio (variable duty ratio) from the CPU 120a to control the supply of electric power to the electric heater 119.

An interface 126 constitutes an output circuit of the CPU 120a, and comprises an output latch memory and a power transistor, etc.

The CPU 120a serves to drive and control the electric load group 108 through the interface 126.

A control power supply 127 is supplied with electric power from the battery 101 through the power supply switch 102 and the power supply terminal 103 to provide a stabilized power supply of DC 5 volts for feeding electric power to the respective circuit elements in the temperature control apparatus 100a.

A sensor interface circuit, generally designated at reference numeral 130a, is connected at its input side to the exhaust gas sensor 107 through the control terminal group 105c, and at its output side to the AD converter 124a.

In the sensor interface circuit 130a, the oxygen concentration reference generation electric current (Icp) supply circuit 131 serves to supply a fine electric current of about 10 μA to 25 μA to the oxygen concentration cell element 111 to set the battery cell element electrode 117b as the oxygen concentration reference.

A battery cell element interterminal voltage detection circuit 132 detects the output voltage Vs that is the interterminal voltage of the oxygen concentration cell element 111.

Here, note that the output voltage Vs becomes a reference voltage of 450 mV at the stoichiometric air fuel ratio A/F (=14.57).

Figure 3:
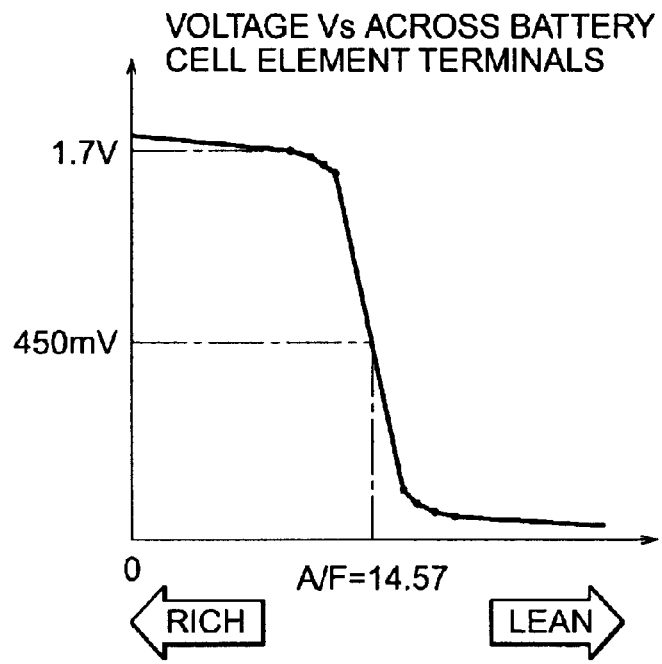
FIG. 3 is an explanatory view illustrating the characteristic of the voltage Vs across battery cell element terminals of the exhaust gas sensor with respect to the air fuel ratio A/F of a mixture according to the first embodiment of the present invention.

FIG. 3 is an explanatory view that shows the output characteristic of the battery cell element interterminal voltage detection circuit 132, wherein the axis of abscissa represents the air fuel ratio (rich, lean or stoichiometric air fuel ratio) and the axis of ordinate represents the battery cell element interterminal voltage Vs.

Turning again to FIG. 1, an internal resistance detection circuit 133 therein detects the internal resistance value R of the oxygen concentration cell element 111. The internal resistance detection circuit 133 regularly performs short time sampling at a cycle of about 100 msec for instance, measures a high-frequency voltage V corresponding to a constant high-frequency current I0 supplied thereto, and calculates an internal resistance value R based on an internal impedance Z0 (=V/I0) in the form of the ratio of the high-frequency voltage V and the constant high-frequency current I0.

It is to be noted that the reason for measuring the internal resistance value R by using the high-frequency current is to remove the influence of the electrode interface resistance. Since an electrostatic capacity component having a relatively large capacity is parasitic in parallel on the electrode interface resistance, as is well known, the electrode interface resistance has such a property of exhibiting a low impedance characteristic with respect to high-frequency current.

Moreover, when a high-frequency current I is measured under the application of a constant high-frequency voltage V0, the calculation of the ratio of an impedance Z (=V0/I) is needed, but if the voltage V supplied when the constant high-frequency current I0 is supplied is measured as described above, the internal impedance Z0 results in a relationship $Z0 (=V/I0) \propto V$, and hence the complicated arithmetic calculations of the ratio become unnecessary.

Figure 4:
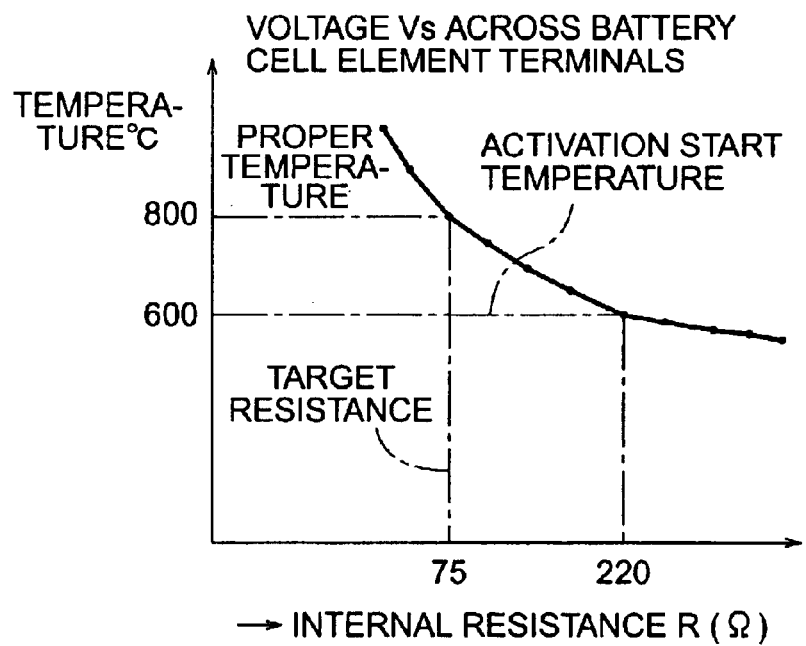
FIG. 4 is an explanatory view illustrating the temperature characteristic of the exhaust gas sensor with respect to the internal resistance value R of an oxygen concentration cell element according to the first embodiment of the present invention.

FIG. 4 is an explanatory view that shows the relation between the internal resistance value R calculated as mentioned above and the temperature of the exhaust gas sensor 107. In FIG. 4, when the temperature of the exhaust gas sensor 107 is the proper activation temperature of 800° C. for instance, which is a control target, the internal resistance value R exhibits 75 Ω.

Reverting to FIG. 1, a reference voltage generation circuit 134 in the sensor interface circuit 130a generates a reference voltage value of 450 mV, which is the target value of the battery cell element interterminal voltage Vs.

A comparison control circuit 135 compares the output voltage of the battery cell element interterminal voltage detection circuit 132 with the reference voltage value from the reference voltage generation circuit 134, and controls the pump current (Ip current) control circuit 136 based on the comparison result.

That is, the comparison control circuit 135 controls the pump current control circuit 136 in such a manner as to make the voltage Vs across the battery cell element terminals detected by the battery cell element interterminal voltage detection circuit 132 equal to the reference voltage value of 450 mV, and detects the value of the oxygen concentration in the gas detection chamber 113 from the value of the pump current Ip required at this time.

Note that the oxygen concentration in the gas detection chamber 113 (corresponding to the air fuel ratio A/F) increases and decreases depending upon the magnitude or polarity (positive or negative) of the pump current Ip supplied from the pump current control circuit 136.

Figure 5:
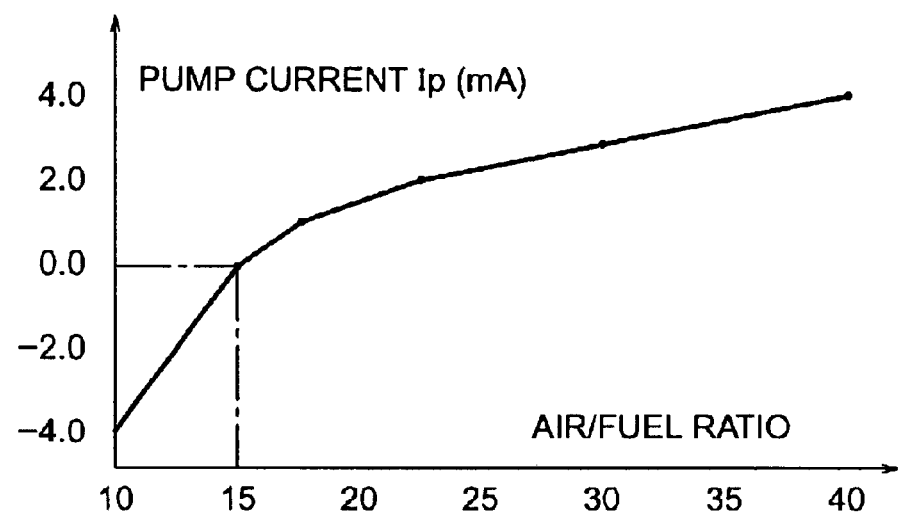
FIG. 5 is an explanatory view illustrating the characteristic of the pump current of the exhaust gas sensor with respect to the air fuel ratio A/F of the mixture according to the first embodiment of the present invention.

FIG. 5 is an explanatory view that shows the relation of the pump current Ip [mA] with respect to the air fuel ratio A/F.

In FIG. 1, a breaks (or open-circuits) and short-circuits detection circuit 137 generates and inputs an abnormality determination signal ER to an ER port of the CPU 120a when it detects a sensor line abnormality (hereinafter simply referred to as a "sensor abnormality") such as a break (i.e., open circuit), a short circuit or the like of the connection wiring between the exhaust gas sensor 107 and the temperature control apparatus 100a. Here, note that the breaks and short-circuits detection circuit 137 may have, in addition to the function of detecting a wiring abnormality, a signal determination function of determining whether each of a variety of signal voltages exceeds a prescribed range (i.e., an upper limit or a lower limit).

The input signals to the CPU 120a include a switch input signal group from the sensor switch group 104 through the DI port, an analog input signal group from the analog sensor group 106 and the exhaust gas sensor 107 through the AI port, and an abnormality determination signal from the breaks and short-circuits detection circuit 137 through the ER port.

In addition, the output signals from the CPU 120a include an energization starting command signal (operation start instruction) from a DRP port to the pump current control circuit 136, a heater drive signal from the DRH port to the switching element 125a, and a load drive signal group from a DR port to the electric load group 108.

Further, the input signals to the multichannel A/D converter 124a include the pump current detection signal Ip from the pump current control circuit 136, the battery cell element interterminal voltage detection signal Vs from the battery cell element interterminal voltage detection circuit 132, an internal resistance detection signal Vr from the internal resistance detection circuit 133, and a power supply voltage Vb from the battery 101.

Next, reference will be schematically made to the operation of the temperature control apparatus for an exhaust gas sensor according to the first embodiment of the present invention, as shown in FIG. 1.

In FIG. 1, when the power supply switch 102 is closed to start the internal combustion engine (not shown), the CPU 120a drives and controls the electric load group 108, the electric heater 119, etc., in accordance with input signals from the sensor switch group 104, the analog sensor group 106 and the exhaust gas sensor 107.

In particular, the CPU 120a performs fuel injection amount feedback control on the unillustrated fuel injection electromagnetic valve included in the electric load group 108 by referring to the value of the pump current detection signal Ip in such a manner that the actually detected air fuel ratio is made to coincide with the target air fuel ratio.

Furthermore, the CPU 120a performs control processing on the switching element 125a for driving the electric heater 119 by using the internal resistance detection signal Vr, the battery cell element interterminal voltage detection signal Vs, and the abnormality determination signal ER (see FIG. 2), whereby the temperature of the exhaust gas sensor 107 is properly controlled.

Now, the concrete operation of the temperature control apparatus 100a according to the first embodiment of the present invention as illustrated in FIG. 1 will be described while referring to the flow chart of FIG. 2.

In FIG. 2, first in step 200, a control operation for the electric heater 119 is started. Then, in step 201, depending upon whether the rotational speed of the internal combustion engine becomes greater than or equal to a predetermined value for instance (or whether an unillustrated starter switch has not been turned on), it is determined whether the starting of the internal combustion engine has been completed.

If it is determined in step 201 that the engine starting has been completed (that is, YES), the control flow proceeds to step 202, whereas if determined that the engine starting has not yet been completed (that is, NO), then the control flow proceeds to step 203 for ending the control operation for the electric heater 119, and the processing routine of FIG. 2 is exited.

In step 202, it is determined whether the power supply voltage Vb of the battery 101 becomes excessive.

If it is determined in step 202 that the power supply voltage Vb is excessive (that is, YES), the control flow proceeds to the operation ending step 203, whereas if determined that the power supply voltage Vb is normal (that is, NO), the control flow proceeds to step 210.

Here, note that the state in which the power supply voltage Vb of the battery 101 becomes excessive corresponds to the state in which electric power is supplied from a charging generator (not shown) with the battery terminals being disconnected.

In addition, in the operation ending step 203, the control flow again proceeds to the operation starting step 200 after the CPU 120a has performed other control operations.

In step 210, depending upon whether a preheating completion flag has already been set (i.e., preheating control has been carried out) in step 219 to be described later, it is determined whether the present operation is a first time operation.

If it is determined in step 210 that the present operation is not a first time operation since the preheating control has been already carried out and preheating has been completed (that is, NO), the control flow proceeds to step 230 (to be described later), whereas if determined that the present operation is a first time operation in which preheating has not yet been performed (that is, YES), the control flow proceeds to step 211.

In step 211, the CPU 120a reads the detected temperature value of the water temperature sensor (i.e., the temperature of internal combustion engine cooling water or cooling water temperature) and the outside or ambient air temperature from the analog sensor group 106.

Subsequently, in step 213, a first preheating time (first period) is decided. At this time, the first preheating time [seconds] as needed is decided depending upon the engine cooling water temperature [° C.] according to the characteristic shown in an explanatory view of FIG. 6.

Figure 6:
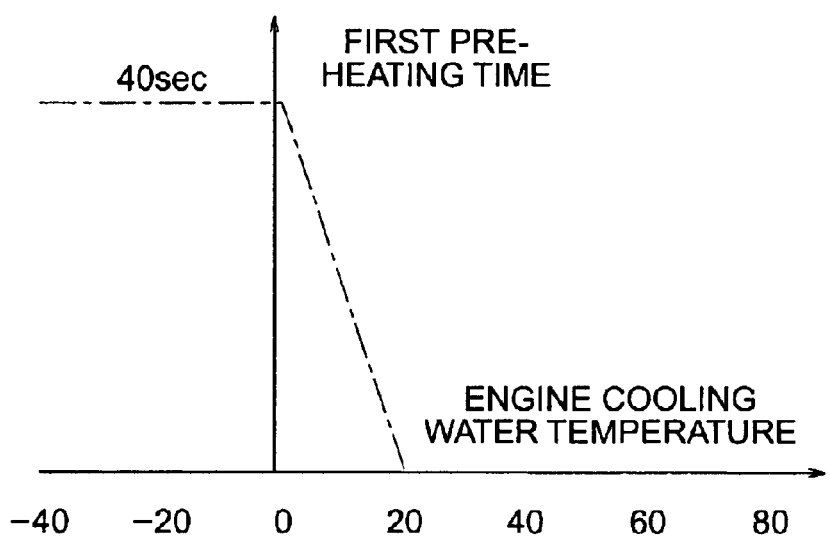
FIG. 6 is an explanatory view illustrating the characteristic of the first effective preheating time of the exhaust gas sensor with respect to the temperature of engine cooling water according to the first embodiment of the present invention.

In FIG. 6, the first preheating time is set to a fixed time (e.g., 40 seconds) when the temperature of cooling water is 0° C. or less, and it is set to a decreasing time as the temperature of cooling water rises in the range of 0° C. to 20° C. On the other hand, the first preheating time is set to 0 seconds when the temperature of cooling water is 20° C. or more. That is, the first preheating time becomes unnecessary if the temperature of engine cooling water is 20° C. or more.

Here, note that in step 213 in FIG. 2, the first preheating time may be set by referring to the outside or ambient air temperature in place of the temperature of engine cooling water, or it may be set based on either one (i.e., the lower one) of the engine cooling water temperature and the outside air temperature. For instance, in cases where warm water is replenished upon cold engine starting, it is preferable to set the first preheating time based on the outside air temperature. That is, it is preferable to perform first preheating energization in step 217 (to be described later) only when it is determined, based on the lower or lowest temperature among the respective environmental temperatures detected by a plurality of environmental temperature measurement means, that the internal combustion engine is at a low temperature.

Subsequent to step 213, the value of the power supply voltage Vb from the battery 101 is read out in step 215, the on/off ratio of the switching element 125a is decided in step 216, and the preheating energization of the electric heater 119 is carried out for the first preheating period in step 217.

At this time, if it is assumed that based on the power supply voltage Vb (for instance 14 V) read out in step 215, the effective voltage applied to the electric heater 119 in the first preheating period in step 217 is represented by V1 (e.g., 3.5 V), and that the on/off cycle or period of the electric heater 119 is represented by T0, the on/off ratio (i.e., the ratio of the on time to the on/off cycle or period T0) decided in step 216 is represented by the following expression (1).

$$V1 = \sqrt{(t \times Vb^2/T0)} \quad (1)$$

$$\therefore (t/T0) = (V1/Vb)^2 \quad (2)$$
$$= (3.5/14)^2$$
$$= 0.0625$$

Accordingly, in step 217, the first voltage (=3.5 V) is applied to the electric heater 119 based on the on/off ratio (=t/T0) decided as shown by expression (2) above, thereby performing the first preheating energization according to the first energization control means.

Subsequently, in step 218, it is determined whether the preheating time (first period) decided in step 213 has elapsed.

If it is determined in step 218 that the preheating time has not yet elapsed (that is, NO), a return is performed to step 217 where the preheating energization is continued, whereas if determined otherwise (that is, YES), the control flow proceeds to step 219 where the preheating completion flag is set up. Note that the temperature level of the electric heater 119 according to the first preheating energization control (step 217) is set to 200° C. for example. This preheating control temperature (200° C.) is a temperature at which the exhaust gas sensor 107 or the electric heater 119 will not be damaged even if the moisture contained in the exhaust gas being adhered to the exhaust gas sensor 107 or the electric heater 119 is rapidly cooled, and at which the condensed water adhered to the exhaust gas sensor 107 or the electric heater 119 can be evaporated.

In step 220 following step 219, it is determined whether the value of the interterminal voltage Vs of the oxygen concentration cell element 111 in the exhaust gas sensor 107 is excessive, i.e., greater than a determination reference value. At this time, the determination reference value as used in step 220 is set to 1.7 V, as shown in FIG. 3 for instance. It is to be noted that since the interterminal voltage Vs of the oxygen concentration cell element 111 has strong temperature dependence and hence in the state of low temperatures, the internal resistance value R of the oxygen concentration cell element 111 is very high, the battery cell element interterminal voltage Vs (=oxygen electromotive force +R× oxygen concentration reference generation electric current) becomes a large value.

If it is determined in step 220 that the battery cell element interterminal voltage Vs is lower than or equal to the determination reference value 1.7 V (that is, NO), the control flow proceeds to step 230 (to be described later), whereas if determined that the battery cell element interterminal voltage Vs is higher than the determination reference value 1.7 V (that is, YES), the control flow proceeds to step 221.

In step 221, it is determined whether the excessive state of the battery cell element interterminal voltage Vs has continued in excess of a second predetermined preheating time (e.g., 5 seconds).

If it is determined in step 221 that the second predetermined preheating time has not yet been exceeded (that is, NO), the control flow proceeds to step 222, whereas if determined otherwise (that is, YES), the control flow proceeds to step 225.

In step 222, an effective power supply voltage V2 to the electric heater 119 is raised to 12 V for instance to intensify or enhance the preheating energization, and then a return to step 220 is carried out.

Thereafter, even if the second preheating energization control according to step 222 is continued, the excessive state of the battery cell element interterminal voltage Vs is not resolved or removed, and hence if it is determined in step 221 that the second predetermined preheating time (5 seconds) has elapsed, the control flow proceeds to step 225 (abnormality flag setting processing). That is, when the battery cell element interterminal voltage Vs does not fall below or equal to the determination reference (1.7 V) even if the second preheating energization control (preheating enhancement) is performed over the second predetermined preheating time (5 seconds), then in step 225, an abnormality flag is set up and the control flow proceeds to step 231 (to be described later).

When it is determined in step 210 that the preheating energization of the electric heater 119 is not a first time operation as previously stated, or when it is determined in step 220 that the battery cell element interterminal voltage Vs in the exhaust gas sensor 107 is not excessive, the determination processing in step 230 is performed.

In step 230, a determination is made as to whether an abnormality determination signal ER from the breaks and short-circuits detection circuit 137 (see FIG. 1) is input to the CPU 120a (sensor abnormal state).

If it is determined in step 230 that there is no sensor abnormality (that is, NO), the control flow proceeds to step 240 (to be described later), whereas if determined otherwise (that is, YES), the control flow proceeds to step 231 where the value of the power supply voltage Vb of the battery 101 is read out.

Subsequently in step 232, the on/off ratio of the switching element 125a is decided in such a manner that an effective voltage V3 (e.g., 11 V) is applied to the electric heater 119.

Thereafter, in step 233, the electric heater 119 is kept heated by using the on/off ratio decided in step 232, and then the control flow proceeds to step 203 where the operation of the processing routine of FIG. 2 is ended.

Here, it is to be noted that the processing of keeping heating the electric heater 119 in step 233 is carried out to prevent poisonous deterioration of the exhaust gas sensor 107 due to phosphorus, sulfur, etc., by continuously heating the exhaust gas sensor 107 even when it becomes impossible to perform fuel injection control (feedback control) using the exhaust gas sensor 107 because of occurrence of a short circuit, an open circuit, a break, etc., in the connecting lines between the exhaust gas sensor 107 and the temperature control apparatus 100a.

When it is determined in step 230 that there is no sensor abnormality, as described above, the step 240 is performed. In step 240, an internal resistance detection signal Vr (internal resistance value R) from the internal resistance detection circuit 133 (see FIG. 1) is read out.

Then, in step 241, it is determined whether the internal resistance value R read out in step 240 is greater than or equal to a first reference value R1 (reference 1) (i.e., target resistance value of 75 Ω in FIG. 4).

If it is determined as R<R1 in step 241 (that is, NO), the control flow proceeds to step 247 (to be described later), whereas if determined as R≧R1 (that is, YES), the control flow proceeds to step 242.

In step 242, it is determined whether the internal resistance value R read out in step 240 is equal to the target resistance value R1 (reference 1) (=75 Ω).

If it is determined as R=R1 in step 242 (that is, YES), the control flow proceeds to the operation ending step 203, whereas if the internal resistance value R is large (i.e., the temperature is low) and hence it is determined as R>R1 (that is, NO), the control flow proceeds to step 243 where the value of the power supply voltage Vb of the battery 101 is read out. Subsequently, in step 244, the on/off ratio of the switching element 125a is incremented by a minute quantity from the present value.

Then, in step 245, it is determined whether the internal resistance value R read out in step 240 has fallen below or equal to a second reference value R2 (reference 2) (e.g., resistance value of 220 Ω in FIG. 4) which corresponding to an activation starting temperature.

If it is determined as R>R2 in step 245 (that is, NO), the control flow proceeds to the operation ending step 203, whereas if determined as R≦R2 (that is, YES), the control flow proceeds to the 246 (energization starting command means) In step 246, an energization starting command signal is generated from the DRP port of the CPU 120a to command or instruct the starting of operation of the pump current control circuit 136, and then the control flow proceeds to the operation ending step 203.

As previously stated, when it is determined in step 241 that the internal resistance value R is less than the first reference value R1 (=75 Ω) (high temperature state), the step 247 is performed. In step 247, the value of the power supply voltage Vb of the battery 101 is read out. Subsequently in step 248, the on/off ratio of the switching element 125a is decreased by a minute quantity from the present value, and the control flow proceeds to the operation ending step 203.

Now, the processing operation shown in FIG. 2 will be explained by replacing the respective steps with means of implementing the respective functions. The step 201 (engine starting completion determination processing) constitutes a "delayed power supplying means" for performing a scavenging operation (i.e., sweeping of initial exhaust gas) during the cranking of the internal combustion engine.

That is, in the cranking period from the beginning of engine starting until the internal combustion engine has been started, the condensed water remaining in the exhaust pipe is scavenged or discharged therefrom, and the supply of electric power to the electric heater 119 is stopped for this period.

The step 217 (first preheating energization control) constitutes a "first preheating means" for evaporating the moisture or condensed water which is generated for a while during cold starting of the internal combustion engine and adhered to the exhaust gas sensor 107 or the electric heater 119.

In addition, the step 213 (preheating time decision processing) constitutes an "effective period setting means" of the first preheating means.

The step 222 (second preheating control: preheating enhancement control) constitutes a "second preheating means" for preventing thermal shock damage due to the rapid heating of the exhaust gas sensor 107 or the electric heater 119.

Moreover, the step 220 (processing of determining excessiveness in the battery cell element interterminal voltage Vs) constitutes a "preheating completion determination means (arithmetic calculation starting determination means)", and the step 221 (elapsed time determination processing) constitutes a "preheating abnormality determination means".

The "preheating completion determination means" (step 220) determines the presence of a preheating abnormality state if preheating has not been completed within the predetermined time, and the "preheating abnormality determination means" (step 221) also determines the presence of a preheating abnormality state if the battery cell element interterminal voltage Vs has not fallen below or equal to the determination reference value (=1.7 V) within the predetermined time.

The step 244 (processing of increasing the on/off ratio of the electric heater 119) and the step 248 (processing of decreasing the on/off ratio of the electric heater 119) together constitute a "heating control means" for performing feedback control in such a manner that the internal resistance value R is controlled to be the target resistance value R1 (=75 Ω) so as to obtain the proper activation temperature (=800° C.) of the exhaust gas sensor 107. That is, when the internal resistance value R as measured is larger than the target resistance value R1 (i.e., indicating a low temperature state), the "heating control means" (steps 244 and 248) serves to gradually increase the voltage supplied to the electric heater 119 by repeatedly performing the step 244.

On the other hand, when the internal resistance value R is less than the target resistance value R1 (i.e., indicating a high temperature state), the "heating control means" serves to gradually decrease the voltage supplied to the electric heater 119 by repeatedly performing the step 248.

The step 233 (heating keeping processing) constitutes a "heating keeping means" and a "heating keeping control means" which serve to keep or continue the operation of the electric heater 119 even if the exhaust gas sensor 107 is disabled due to the occurrence of a wiring abnormality of the exhaust gas sensor 107 or the occurrence of a preheating abnormality in step 221.

Here, note that since the heating keeping means responding to a sensor abnormality and the heating keeping control means responding to a preheating abnormality are constituted by one and the same processing block (step 233), the step 233 (the heating keeping means and the heating keeping control means) is hereinafter simply and generically called a "heating keeping means".

The heating keeping means and the heating keeping control means (step 233) serve to prevent the exhaust gas sensor 107 from being deteriorated by exhaust gas components by keeping the exhaust gas sensor 107 in an elevated temperature environment.

As described above, the electric power supplied to the electric heater 119 installed in the neighborhood of the exhaust gas sensor 107 is controlled through the switching element 125a by the CPU 120a which cooperates with the ROM (nonvolatile memory) 121a. That is, a low voltage for evaporation of the pour or condensed water is supplied by the first preheating means immediately after the starting of the internal combustion engine, and subsequently, enhanced preheating for prevention of thermal shock is carried out by the second preheating means. Thereafter, the heating control means performs automatic feedback control while making the proper activation temperature (=800° C.) of the exhaust gas sensor 107 as the target temperature.

At this time, since the first preheating means is set to such a temperature level at which damage due to rapid cooling of the pour or condensed water will not be generated but the pour or condensed water can be evaporated to a satisfactory extent, it is possible to achieve heating control on the exhaust gas sensor 107 having the electric heater 119 in such a manner that the exhaust gas sensor 107 is able to promptly reach the proper activation temperature while preventing the pour water rapid cooling damage and rapid heating damage thereof immediately after engine starting.

That is, in FIGS. 1 and 2, provision is made for the first preheating means (step 217), the second preheating means (step 222), the temperature detection means (steps 220 and 241) and the heating control means (steps 244 and 248), the first preheating means applies the first low voltage to the electric heater 119 during the first period in order to evaporate the condensed water adhered to the exhaust gas sensor 107, and the second preheating means applies the second low voltage, which is higher than the first low voltage, to the electric heater 119 in the second period following the first period so as to avoid rapidly supplying maximum electric power thereto.

Furthermore, the temperature detection means detects the internal resistance value R of the exhaust gas sensor 107 or the resistance value Rh of the electric heater 119, and determines whether the exhaust gas sensor 107 is in a temperature state in the vicinity of the activation temperature thereof. The heating control means assumes the proper activation temperature of the exhaust gas sensor 107 to be the target temperature, and controls the conductive state of the switching element 125a in a feedback manner depending upon the correlation characteristic between the target temperature and the resistance detected by the temperature detection means.

In addition, the preheating energization of the electric heater 119 by the first and second preheating means is performed prior to the feedback control. Therefore, the rapid cooling damage of the exhaust gas sensor 107 due to condensed water or thermal shock damage thereof due to rapid heating can be prevented, thereby making it possible to prolong the service life of the exhaust gas sensor 107 with the electric heater 119 as well as to promptly control the temperature of the exhaust gas sensor 107 to the proper activation temperature thereof.

Moreover, the first preheating means includes the delayed power supply means (step 201) which starts operating after a prescribed scavenging period has elapsed from the beginning of starting the internal combustion engine, whereby it is possible to avoid preheating immediately after the engine starting in which excessive moisture is contained in the exhaust gas. That is, even when there is a possibility of excessive condensed moisture being contained in the exhaust gas owing to the residual moisture remaining after the last engine stop, preheating energization immediately after the present engine starting is avoided only for a while, so that the load on the battery 101 can be reduced to increase or enhance electric power supply to an electric starter motor of the internal combustion engine. At this time, the scavenging period is set as a period which is proportional to the starting or cranking period of the internal combustion engine or a period in which the total amount of intake air sucked into the internal combustion engine reaches a predetermined value. For instance, taking account of the fact that a longer starting time or period is required upon the cold start of the internal combustion engine in which the exhaust gas is apt to contain an increased amount of condensed water, it is possible to ensure a balanced scavenging time by setting the scavenging period in proportion to the engine cranking period.

Further, by setting, as the scavenging period, the period within which the total amount of intake air reaches a predetermined value so that a prescribed amount of exhaust gas is discharged at the time of engine starting, it is possible to start the first preheating after the residual condensed water has been scavenged or removed without fail.

Furthermore, the first preheating means includes the effective period setting means (step 213), which serves to make the first preheating means effective during a predetermined effective period depending upon an environmental temperature (i.e., engine ambient temperature) at starting of the internal combustion engine, and also makes the second preheating means or the heating keeping means (step 233) effective in accordance with the lapse of the effective period. Therefore, the heating keeping means serves to suppress impurities from adhering to the exhaust gas sensor 107 even during nonuse of the exhaust gas sensor 107, thus making it possible to prevent poisonous deterioration of the exhaust gas sensor 107.

Additionally, the first preheating operation can be completed in as short a time as possible, and it is also possible to promptly start the second preheating operation under a high temperature environment while omitting the first preheating operation. At this time, the environmental temperature (i.e., engine ambient temperature) is decided depending upon the lower one of the engine cooling water temperature and the outside air temperature. Accordingly, even when warm water is replenished as cooling water in order to facilitate the starting of the internal combustion engine for instance, the first preheating time is not shortened abnormally, thus making it possible to improve the reliability of the preheating energization control.

In addition, provision is made for the preheating completion determination means (step 220) for determining the completion of the preheating of the second preheating means, and the preheating completion determination means determines the completion of preheating when the interterminal voltage Vs of the oxygen concentration cell element 111 has fallen below or equal to a predetermined value, and makes the heating control means effective after the completing of preheating. Therefore, it is possible to promptly shift temperature control on the exhaust gas sensor to the normal temperature control state by accurately determining the time point of the completion of preheating.

Moreover, provision is also made for the preheating abnormality detection means (steps 221 and 225) which is able to detect that the interterminal voltage Vs of the oxygen concentration cell element 111 does not fall below or equal to the predetermined value even if a predetermined time has elapsed after the start of preheating by the second preheating means.

When the preheating abnormality detection means has detected abnormality, the heating keeping means is made effective following the first preheating means, so that it continuously controls the energization to the electric heater at a low voltage higher than the first voltage, thereby suppressing impurities from adhering to the exhaust gas sensor 107. Thus, even when there takes place abnormal preheating due to an abnormality in the battery cell element interterminal voltage detection circuit 132, an abnormality in the wiring for the exhaust gas sensor 107 or the like, the heating keeping means serves to suppress poisonous deterioration of the exhaust gas sensor 107 resulting from the adhesion of impurities thereto.

Further, the temperature detection means detects the temperature of the exhaust gas sensor 107 based on the internal resistance value R calculated from the ratio of a constant high-frequency current that is regularly sampled and supplied to the oxygen concentration cell element 111 to a high-frequency voltage corresponding to the high-frequency current.

Furthermore, the temperature detection means includes the arithmetic calculation starting determination means for calculating the internal resistance value R, and the arithmetic calculation starting determination means starts the calculation of the internal resistance value R from the time point at which the preheating completion determination means determines the completion of the second preheating energization. Accordingly, the internal resistance value R of the exhaust gas sensor 107 can be measured in an easy and accurate manner, and unnecessary measurements can be avoided.

Still further, the temperature detection means includes the pump current energization starting command means (steps 245 and 246), which starts supplying a pump current to the oxygen pump element 110 at the time when the temperature detection means reaches the activation starting temperature lower than the proper activation temperature of the exhaust gas sensor 107. Thus, the temperature detection means can promptly start supplying the pump current to the oxygen pump element 110 when the exhaust gas sensor 107 has reached the activation starting temperature lower than the proper activation temperature thereof.

In addition, the CPU 120a that controls the on/off ratio of the switching element 125a has the fuel injection control function of controlling fuel injection to the internal combustion engine. Thus, the entire apparatus can be reduced in size and produced at low cost as compared with the case where the temperature control apparatus is constructed separately or independently.

Embodiment 2.

Although in the above-mentioned first embodiment, the internal resistance value R of the exhaust gas sensor 107 is measured or calculated so as to detect the temperature of the exhaust gas sensor 107, the temperature of the exhaust gas sensor 107 may be detected based on a heater resistance value which is calculated from the current supplied to the electric heater 119.

Figure 7:
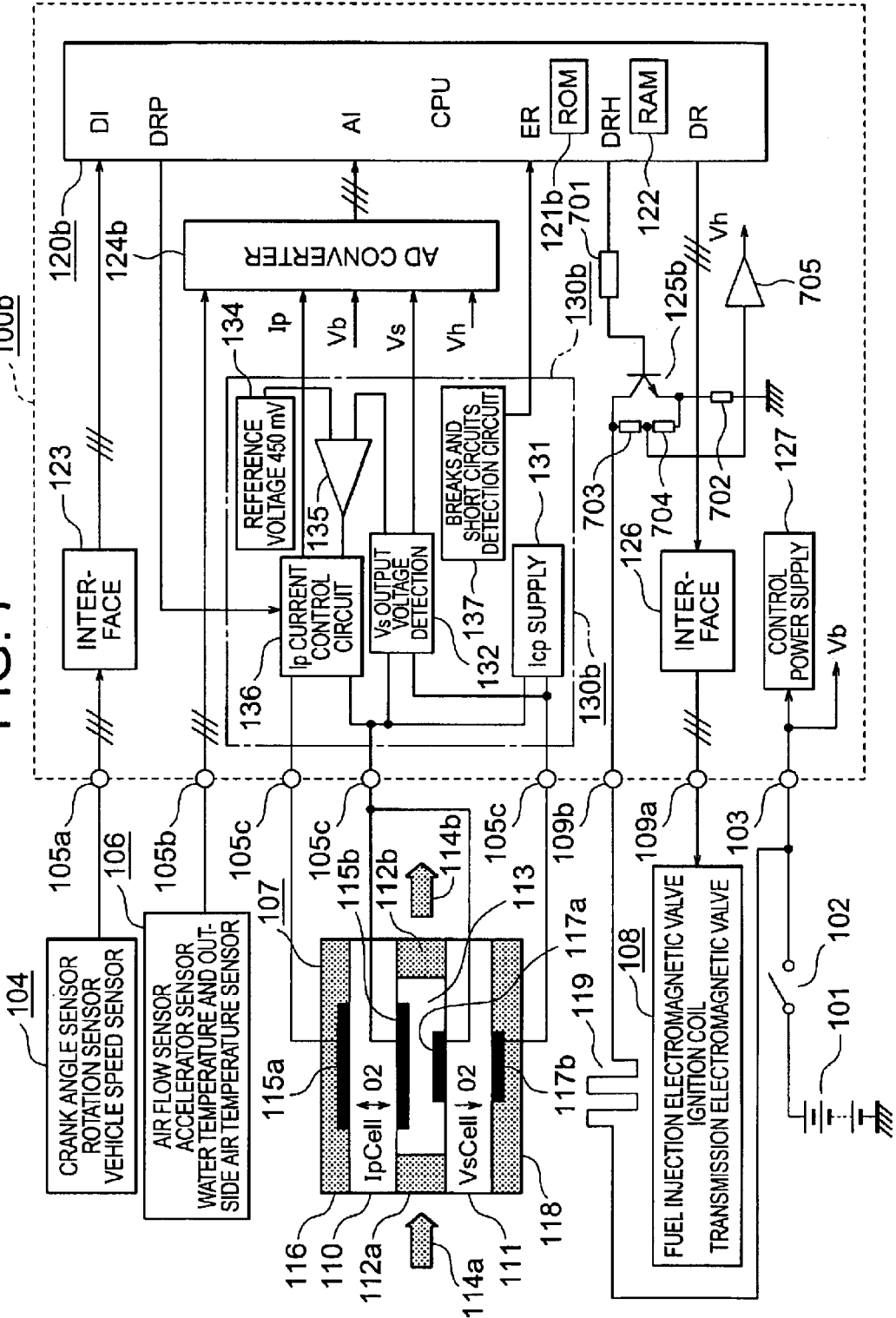
FIG. 7 is a block diagram showing a temperature control apparatus for an exhaust gas sensor according to a second embodiment of the present invention.

Hereinafter, reference will be made to a temperature control apparatus according to a second embodiment of the present invention, which is constructed to detect the temperature of the exhaust gas sensor 107 by using a heater current detection signal Vh, while referring to a block diagram of FIG. 7. In FIG. 7, the same or like parts or elements as those described above (see FIG. 1) are identified by the same symbols while omitting a detailed description thereof.

In this case, the temperature control apparatus, generally designated at reference numeral 100b, is provided, as component elements corresponding to those of the aforementioned one (see FIG. 1), with a CPU or microprocessor 120b which cooperates with a ROM (program memory) 121b, a multichannel A/D converter 124b, a switching element 125b in the form of a power transistor, and a sensor interface circuit 130b connected to the exhaust gas sensor 107. The sensor interface circuit 130b in FIG. 7 is different from the above-mentioned sensor interface circuit 130a (see FIG. 1) in the absence of the internal resistance detection circuit 133.

The temperature control apparatus 100b is provided, in addition to the above component elements, with circuit elements 701 through 705 which are related to the switching element 125b. The respective circuit elements 701 through 705 constitute a heater current detection circuit that generates a heater current detection signal Vh.

A driving resistor 701 is connected at one end thereof with a base terminal of the switching element 125b, and at the other end thereof with a heater drive signal terminal (DRH port) of the microprocessor 120b.

An energization current detection resistor 702 is inserted between an emitter terminal of the switching element 125b and ground.

A pair of voltage divider resistors 703, 704 are connected in series with each other, and inserted between the emitter terminal and the collector terminal of the switching element 125b to form an open-circuit or break detection circuit.

An amplifier 705 functions as an output circuit of the heater current detection circuit to amplify the potential at a junction between the voltage divider resistors 703, 704 and output it as a heater current detection signal Vh. The heater current detection signal Vh is input to an AI port of the CPU 120b through the A/D converter 124b.

Now, reference will be made to the concrete processing operation of the temperature control apparatus 100b according to the second embodiment of the present invention as illustrated in FIG. 7 while referring to a flow chart of FIG. 8 together with the explanatory views of FIGS. 3 and 6.

Figure 8:
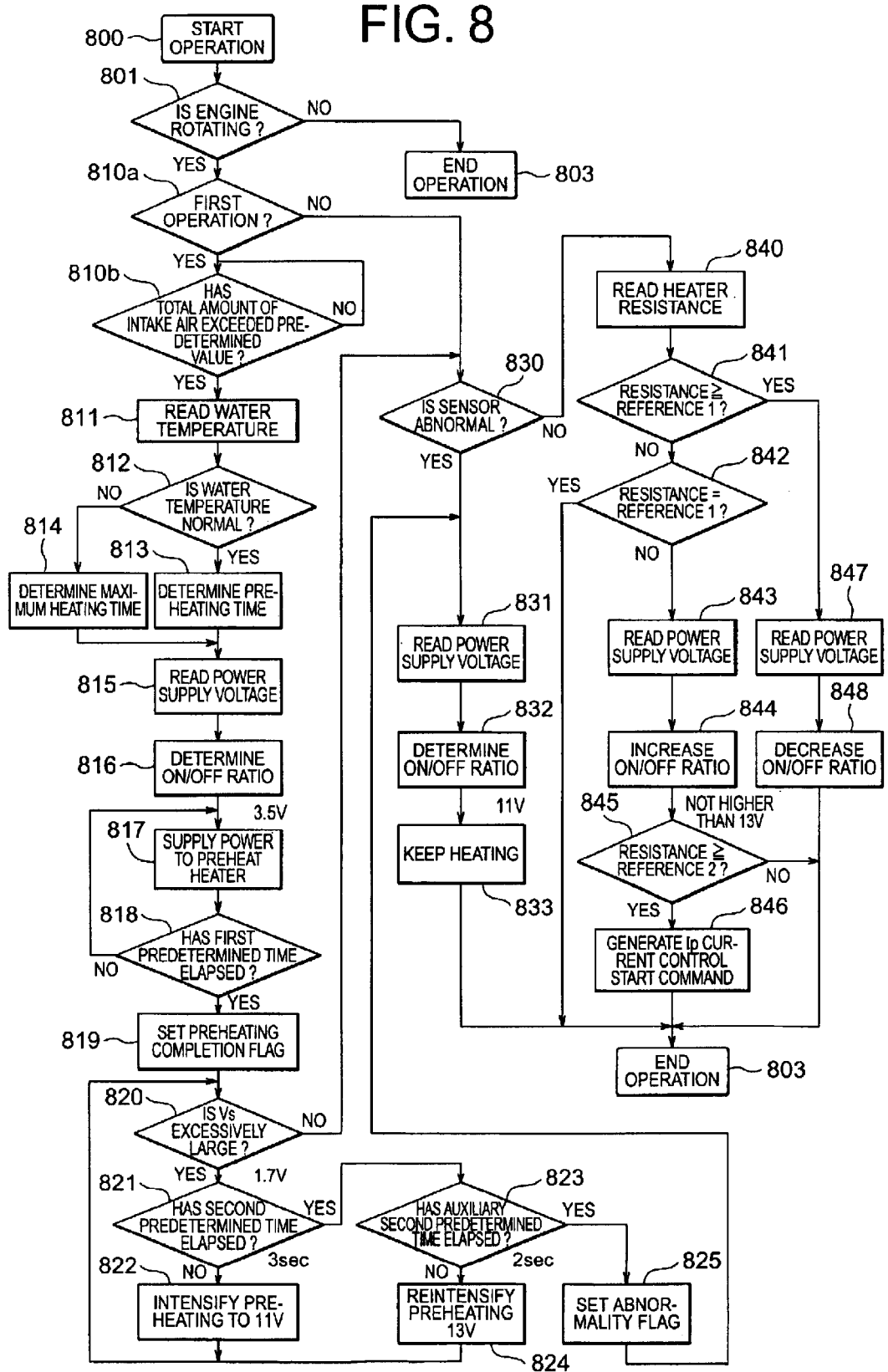
FIG. 8 is a flow chart illustrating the operation of the temperature control apparatus for an exhaust gas sensor according to the second embodiment of the present invention.

In FIG. 8, steps 800 through 848 correspond to above-mentioned steps 200 through 248 (see FIG. 2), respectively. In this case, however, preheating enhancement control of two stages (11 V and 13 V) is usually carried out in steps 822, 824, as will be described later.

In addition, in step 840 (to be described later), the resistance value of the electric heater 119 is calculated in place of the internal resistance value R of the exhaust gas sensor 107. In this case, since the internal resistance value of the electric heater 119 increases as the temperature thereof rises, contrary to the internal resistance value of the exhaust gas sensor 107 (which decreases in accordance with the rising temperature), the increase and decrease control of the on/off ratio in accordance with the result of determination in step 841 becomes the reverse of what has been stated before (FIG. 2).

First of all, when the control operation of the electric heater 119 is started in step 800, it is then determined in step 801 whether the internal combustion engine is rotating. If it is determined that the internal combustion engine is not rotating or is in a stand still (that is, NO), the control flow proceeds to an operation ending step 803 where the processing routine of FIG. 8 is exited. Here, note that in the operation ending step 803, the control flow again proceeds to the operation starting step 800 after the CPU 120b has carried out other control operations.

If, however, it is determined in step 801 that the internal combustion engine is rotating (that is, YES), the control flow proceeds to step 810a where a determination as to whether the present engine starting operation is a first time operation is made based on the set state of a preheating completion flag in step 819 (to be described later).

If it is determined in step 810a that the preheating completion flag is in a set state (i.e., preheating has been completed) and hence the present engine starting operation is not a first time operation (that is, NO), the control flow proceeds to step 830 (to be described later), whereas if determined that the preheating completion flag is not set (i.e., preheating control has not yet been made) and hence the present engine starting operation is a first time operation (that is, YES), the control flow proceeds to step 810*b*.

In step 810*b*, the amount of intake air into the internal combustion engine measured by an air flow sensor in an analog sensor group 106 (see FIG. 7) is integrated to provide a total amount of intake air, and it is then determined whether the total amount of intake air thus obtained has reached a predetermined value.

If it is determined in step 810*b* that the total amount of intake air has not yet reached the predetermined value (that is, NO), the step 810*b* is performed again, whereas if determined that the total amount of intake air has reached the predetermined value (that is, YES), the control flow proceeds to step 811. In step 811, the temperature of engine cooling water is read from the water temperature sensor.

Subsequently, in step 812, it is determined whether the temperature value of engine cooling water read from the water temperature sensor is normal.

If it is determined in step 812 that the temperature value of engine cooling water is normal (that is, YES), the control flow proceeds to step 813, whereas if determined otherwise (that is, NO), the control flow proceeds to step 814. In step 813, a first preheating time required is decided according to the characteristic shown in FIG. 6. On the other hand, in step 814, the first preheating time is set to a specific preheating time (=40 seconds) in the lowest temperature state (see FIG. 6) since it was determined in step 812 that the temperature value of engine cooling water is abnormal. Here, note that when the input signal value exceeds a prescribed range (i.e., an upper limit or a lower limit) due, for instance, to an open circuit, a short circuit, etc., of the input circuit of the water temperature sensor, it is determined in the determination step 812 that the temperature value of engine cooling water is abnormal.

In step 815 following the step 813 or 814, the value of the power supply voltage Vb of the battery 101 is read out.

In step 816, the on/off ratio of the switching element 125*b* is decided. At this time, the on/off ratio (t/TO) decided in step 816 is represented by the above-mentioned expressions (1) and (2) by using the power supply voltage Vb of the battery 101 (e.g., 14 V) and the effective voltage V1 (e.g., 3.5V) supplied to the electric heater 119 during the first preheating period in step 817 (to be described later), as in the above-mentioned step 216 (FIG. 2).

Subsequently, in step 817, first preheating energization of the electric heater 119 is performed based on the on/off ratio decided in step 816. Then, in step 818, it is determined whether the first preheating time decided in step 813 or 814 has elapsed. If it is determined in step 818 that the first preheating time has not yet elapsed (that is, NO), a return is performed to step 817 where the first preheating energization is continued, whereas if determined that the first preheating time has elapsed (that is, YES), the control flow proceeds to step 819 where a preheating completion flag is set.

Here, note that the control temperature of the electric heater 119 in step 817 (first preheating energization) is set at such a level (e.g., 200° C.) that the exhaust gas sensor 107 and the electric heater 119 will not be damaged even if the moisture contained in the exhaust gas and attached to them is rapidly cooled, and that the condensed water adhering to them can be evaporated.

Since the battery cell element interterminal voltage Vs has high temperature dependence and hence the internal resistance value R of the exhaust gas sensor 107 in the state of low temperatures is very high as described above, the interterminal voltage Vs (=oxygen electromotive force + oxygen concentration reference generation electric current × internal resistance value R) becomes large.

If it is determined in step 820 that the exhaust gas sensor 107 is in the state of low temperatures and the battery cell element interterminal voltage Vs is too high (Vs >1.7 V) (that is, YES), the control flow proceeds to step 821 where it is determined whether a second predetermined preheating time (e.g., 3 seconds) has elapsed.

If it is determined in step 821 that the second predetermined preheating time has not yet elapsed (that is, NO), the control flow proceeds to step 822, whereas if determined otherwise (that is, YES), the control flow proceeds to step 823.

In step 822, the effective power supply voltage to the electric heater 119 is increased from V1 (=3.5 V) to V2a (e.g., 11 V), and then a return to the determination step 820 is carried out.

On the other hand, when the second predetermined preheating time has elapsed, then in step 823, it is determined whether a second predetermined auxiliary preheating enhancement time (e.g., 2 seconds) has elapsed.

If it is determined in step 823 that the second predetermined auxiliary preheating enhancement time has not yet elapsed (that is, NO), the control flow proceeds to step 824, whereas if determined otherwise (that is, YES), the control flow proceeds to step 825.

In step 824, the effective power supply voltage to the electric heater 119 is increased to V2b (e.g., 13 V), and then a return to the determination step 820 is carried out.

In step 825, an abnormality flag is set, and the control flow proceeds to step 831 (to be described later). That is, in cases where the battery cell element interterminal voltage Vs does not fall below or equal to a predetermined value (1.7 V) even if the second preheating energization is continued for a predetermined time (e.g., 3 seconds) in step 822 or even if the second auxiliary preheating energization is continued for a predetermined time (2 seconds) in step 824, it is assumed that the battery cell element interterminal voltage detection circuit 132 is abnormal or connection wiring therefor is abnormal, and hence an abnormality flag is set.

As described above, when it is determined in step 810*a* that the present engine starting operation is a first time operation, or when it is determined in step 820 that the battery cell element interterminal voltage Vs is not excessive, the control flow proceeds to step 830 where it is determined whether an abnormality determination signal ER has been input to the CPU 120*b* from the breaks and short-circuits detection circuit 137 in FIG. 7 (sensor abnormal state).

If it is determined in step 830 that an abnormality determination signal ER has not been input (that is, NO), the control flow proceeds to step 840 (temperature detection means for detecting the temperature of the exhaust gas sensor 107 based on the calculation of the heater resistance value), whereas if determined otherwise (that is, YES), the control flow proceeds to step 831. In step 831, the value of the power supply voltage Vb of the battery 101 is read out.

Subsequently in step 832, the on/off ratio of the switching element 125*b* is decided in such a manner that the effective voltage V3 (e.g., 11 V) is applied to the electric heater 119.

Thereafter, in step 833, the electric heater 119 is kept heated by using the on/off ratio decided in step 832, and then the control flow proceeds to step 803. Here, it is to be noted that similar to the above-mentioned step 233 (FIG. 2), the step 833 is to prevent the poisonous deterioration of the exhaust gas sensor 107 by continuously heating the exhaust gas sensor 107 even when it becomes impossible to perform fuel injection feedback control using the exhaust gas sensor 107 because of the occurrence of a short circuit, an open circuit, a break, etc., in the connecting lines between the exhaust gas sensor 107 and the temperature control apparatus 100b.

When it is determined in step 830 that there is no sensor abnormality, then in step 840, the internal resistance value Rh of the electric heater 119 is calculated as shown in a flow chart of FIG. 9 (to be described later).

Subsequently, in step 841, it is determined whether the internal resistance value Rh read out in step 840 exceeds a first target resistance value Rh1 (reference 1).

If it is determined as Rh>Rh1 in step 841 (that is, YES), the control flow proceeds to step 847 (to be described later), whereas if determined as Rh≦Rh1 (that is, NO), the control flow proceeds to step 842.

In step 842, it is determined whether the internal resistance value Rh calculated in step 840 is equal to the first target resistance value Rh1 (reference 1), and if determined as Rh=Rh1 (that is, YES), the control flow immediately advances to the operation ending step 803.

On the other hand, if determined as Rh<Rh1 in step 842 (that is, NO), it is assumed that the internal resistance value Rh of the electric heater 119 is too small (i.e., the temperature of the exhaust gas sensor 107 is too low), and the control flow proceeds to step 843. In step 843, the value of the power supply voltage Vb of the battery 101 is read out.

Subsequently, in step 844, the on/off ratio of the switching element 125b is incremented by a minute quantity from the present value.

Then, in step 845, it is determined whether the internal resistance value Rh calculated in step 840 has increased above or equal to a second target resistance value Rh2 (reference 2) corresponding to the activation starting temperature, and if determined as Rh<Rh2 (that is, NO), the control flow immediately advances to the operation ending step 803.

If, however, determined as Rh≧Rh2 in step 845 (that is, YES), then in step 846 (energization starting command means), an energization starting command signal is generated from the DRP port (see FIG. 7), whereby the pump current control circuit 136 is commanded to start operating, and the control flow advances to the operation ending step 803.

On the other hand, when determined as Rh>Rh1 (high temperature state) in the above-mentioned step 841, the control flow proceeds to step 847 where the value of the power supply voltage Vb of the battery 101 is read out.

Subsequently in step 848, the on/off ratio of the switching element 125b is decreased by a minute quantity from the present value, and the control flow proceeds to the operation ending step 803.

Here, explaining the processing operation shown in FIG. 8 by replacing the steps with means for performing the respective functions, the step 810b (processing for determining the total amount of intake air) corresponds to the above-mentioned step 201 (FIG. 2) and constitutes a delayed power supply means for scavenging operation.

That is, in a period from the time when the internal combustion engine is started until the total amount of intake air reaches a predetermined value, the condensed water remaining in the exhaust pipe is scavenged or discharged therefrom, and the supplying of power to the electric heater 119 is stopped.

The step 817 constitutes, similar to the above-mentioned step 217 (FIG. 2), a first preheating means for evaporating moisture when the exhaust gas sensor 107 or the electric heater 119 is covered with the condensed water during cold starting.

In addition, the step 813 or the step 814 constitutes an effective period setting means for setting the effective period of the first preheating means, and the step 814 also constitutes a maximum preheating time setting means.

The step 822 constitutes, similar to the above-mentioned step 222 (FIG. 2), a second preheating means for preventing thermal shock damage of the exhaust gas sensor 107 or the electric heater 119 due to the rapid heating thereof.

Also, the step 824 (second auxiliary preheating energization control) constitutes a gradually increasing preheating enhancement means (preheating reintensification or reenhancement means) which is included in the second preheating means.

The step 820 constitutes a preheating completion determination means (arithmetic calculation starting determination means), as in the case of the above-mentioned step 220 (FIG. 2).

Further, the step 823 (elapsed time determination processing) constitutes a preheating abnormality determination means, as in the case of the above-mentioned step 221 (FIG. 2)

The steps 844 and 848 constitute a heating control means that performs feedback control for obtaining the first target resistance value Rh1 (sensor temperature of 800° C.), as in the case of the above-mentioned steps 244 and 248 (FIG. 2). That is, when the internal resistance value Rh of the electric heater 119 measured in step 840 is less than the first target resistance value Rh1 (i.e., low temperature state), the step 844 is repeatedly carried out to gradually increase the voltage supplied to the electric heater 119.

On the other hand, when the internal resistance value Rh is greater than the first target resistance value Rh1 (i.e., high temperature state), the step 848 is repeatedly carried out to gradually decrease the voltage supplied to the electric heater 119.

The step 833 constitutes a heating keeping means and a heating keeping control means, as in the case of the above-mentioned step 233 (FIG. 2), and serves to keep or continue the operation of the electric heater 119 thereby to prevent deterioration of the exhaust gas sensor 107 even if the exhaust gas sensor 107 is disabled due to the occurrence of a wiring abnormality of the exhaust gas sensor 107 or the occurrence of a preheating abnormality in step 823.

Next, a concrete description will be made to the processing of calculating the internal resistance value Rh of the electric heater 119 in step 840 in FIG. 8 while referring to the flow chart of FIG. 9.

In FIG. 9, first of all, an operation is started in step 840a. The step 840a is made effective when it was determined in step 830 in FIG. 8 that there is no sensor abnormality.

Subsequently, in step 901, it is determined whether the electric heater 119 is abnormal. The heater abnormality determination processing in step 901 is performed depending upon whether an abnormality flag is stored in step 905 or 907 (to be described later).

If it is determined in step 901 that the electric heater 119 is abnormal (that is, YES), the control flow advances to the operation ending step 803 in FIG. 8, whereas if determined that the electric heater 119 is not abnormal (that is, NO), the control flow proceeds to step 902a where a heater current detection signal Vh generated when the switching element 125b is conductive or closed is temporarily stored. Then, in step 902b, the power supply voltage Vb is temporarily stored.

Subsequently, in step 902c, the power supply voltage Vb temporarily stored in step 902b is divided by a heater current Ih, which is based on the heater current detection signal Vh temporarily stored in step 902a, to calculate the heater resistance value Rh (=Vb/Ih) of the electric heater 119.

Thereafter, in step 903, it is determined whether the heater resistance value Rh calculated in step 902c is between an upper limit value and a lower limit value (i.e., within a prescribed range).

If it is determined in step 903 that the heater resistance value Rh is within the prescribed range (that is, YES), it is assumed that the electric heater 119 is in a normal state, and the control flow proceeds to step 840b where a return to step 841 in FIG. 8 is performed.

On the other hand, if determined otherwise in step 903 (that is, NO), it is assumed that the electric heater 119 is in an abnormal state, and the control flow proceeds to step 904 where it is determined whether the abnormal state of the electric heater 119 is an excessively large heater resistance abnormality or an excessively small heater resistance abnormality.

If it is determined in step 904 that it is an excessively large heater resistance abnormality such as an open circuit or a break in the heater circuit (that is, YES), the control flow proceeds to step 905, whereas if determined as an excessively small heater resistance abnormality (that is, NO), the control flow proceeds to step 907.

In step 905, the open-circuit or break abnormality is stored, whereas in step 907, the short-circuit abnormality is stored, and the control flow then proceeds to step 906. In step 906, the heater drive signal output from the DRH port of the microprocessor 120b to the switching element 125b is stopped, and then the control flow advances to the operation ending step 803 in FIG. 8.

Here, it is to be noted that the step 902c in FIG. 9 constitutes a heater resistance value measurement means (temperature detection means) for indirectly detecting the temperature of the exhaust gas sensor 107. In addition, the step 905 constitutes an open-circuit detection storage means, the step 907 constitutes a short-circuit detection storage means, and the step 906 constitutes a driving stopping means.

In this manner, the first and second preheating means, which have mutually different purposes, are made effective in the first period and the second period, respectively, before feedback temperature control is performed on the electric heater 119 for activating the exhaust gas sensor 107 at an early stage.

Moreover, provision is made for a means which serves not only to gradually increase the electric power supplied to the electric heater 119 but also to decide the first period and the second period.

Further, in addition to the first preheating means and the heating keeping means, provision is made for a sensor abnormality detection means which generates an abnormality determination signal when temperature control according to the electric heater 119 becomes impossible due to a cut, a break, a short-circuit or the like of the wiring for the exhaust gas sensor 107. Thus, upon detection of an abnormality by the sensor abnormality detection means, the heating keeping means is operated following the first preheating means to continuously apply a prescribed low voltage higher than the first voltage to the electric heater 119, whereby it can suppress impurities from adhering to the exhaust gas sensor 107 even during nonuse of the exhaust gas sensor 107, thus making it possible to prevent poisonous deterioration of the exhaust gas sensor 107.

Furthermore, the second preheating means includes a stepwise preheating keeping means (steps 822 and 824) for variably increasing the second voltage with the lapse of time (e.g., 11 V →13 V). Accordingly, the temperature of the exhaust gas sensor 107 can be raised to its proper activation temperature more promptly, and it is possible to further reduce the heating stress on the exhaust gas sensor 107 and the electric heater 119.

Besides, the effective period setting means includes the maximum preheating time setting means (step 814), and sets the first preheating time to a prescribed maximum time when an environmental temperature at the time of engine starting can not be normally read out, whereby it is possible to improve the safety in operation of the apparatus.

In addition, the temperature detection means estimates the temperature of the exhaust gas sensor 107 based on the heater resistance value Rh of the electric heater 119 detected by the resistance value measurement means, and includes the driving stopping means (step 906) and at least one of the short-circuit detection storage means (step 907) and the open-circuit detection storage means (step 905). Here, note that when the electric current supplied when the switching element 125b for supplying electric power to the electric heater 119 is driven into a conductive state exceeds a predetermined value, the short-circuit detection storage means determines that the electric heater 119 or the power supply circuit therefor is in a short-circuit state, and stores this determination. On the other hand, when the electric current supplied to the open-circuit detection resistors 703, 704 upon interruption or opening of the switching element 125b is below or equal to the predetermined value, the open-circuit detection storage means determines that the electric heater 119 or the power supply circuit therefor is in an open-circuit state, and stores this determination.

Moreover, the driving stopping means stops the supply of electric power to the electric heater 119 at least when the short-circuit detection storage means stores a short-circuit abnormality, so that the electric heater 119 or the switching element 125b can be prevented from being damaged. In this case, too, the preheating abnormality detection means detects that the interterminal voltage Vs of the oxygen concentration cell element 111 does not fall below or equal to the predetermined value even when the predetermined time has elapsed after the start of preheating by the second preheating means.

Further, when an abnormality (e.g., an abnormality of the battery cell element interterminal voltage detection circuit 132, an abnormality in the wiring for the exhaust gas sensor 107, etc.) is detected by the preheating abnormality detection means, the heating keeping means is operated following the first preheating means to continuously apply the prescribed low voltage higher than the first voltage to the electric heater 119, thereby suppressing the poisonous deterioration of the exhaust gas sensor 107 resulting from the adhesion of impurities thereto.

Here, it is to be noted that the temperature control apparatuses 100a, 100b according to the above-mentioned first and second embodiments, respectively, are each constructed as partial functions of a total or entire control system for an internal combustion engine (including fuel injection control, ignition control, etc.), and the power supply control on the electric heater 119 is executed by a microprocessor for use with the fuel injection control for example. However, such control may be effected by an independent microprocessor or a hardware circuit which is comprised of an integrated circuit element having the control circuit for the electric heater 119 integrated with and incorporated in the sensor interface circuit 130*a* or 130*b*.

Although in the above-mentioned first and second embodiments, the linear sensor having the pump current control circuit 136 is used as the exhaust gas sensor 107, such an exhaust gas sensor 107 may be constructed of a limiting current type nonlinear sensor or a nonlinear sensor using the oxygen concentration cell element 111 alone.

Furthermore, in the case of using the nonlinear sensor having the oxygen concentration cell element 111 alone as the exhaust gas sensor 107, by observing or monitoring the battery cell element interterminal voltage Vs, it is possible to know or detect whether the present actual air fuel (A/F) ratio of a mixture is greater than or equal to the stoichiometric air fuel ratio (A/F ratio=14.57). Thus, the fuel injection control can be carried out in such a manner that the amount of fuel to be injected is controlled to increase or decrease on the basis of the stoichiometric air fuel ratio.

Although there are variations in the internal resistance value R of the exhaust gas sensor 107 or in the internal resistance value Rh of the electric heater 119 between products, control accuracy can be improved using a correction means in combination by measuring the initial value of the internal resistance value R or Rh and storing it as a learning value.

In addition, it is also possible to add a function of detecting the deterioration of the exhaust gas sensor 107 based on the aging of the learning value as stored, a function of storing an abnormal state upon occurrence of an abnormality and providing a warning indication, etc.

Although in the above-mentioned first and second embodiments, provision is made for the first and second preheating means and the heating keeping means, which is operated in response to the detection of an abnormality of the exhaust gas sensor 107 or the like, only the first preheating means and the heating keeping means may be provided while omitting the second preheating means.

While the invention has been described in terms of preferred embodiments, those skilled in the art will recognize that the invention can be practiced with modifications within the spirit and scope of the appended claims.

What is claimed is:

1. A temperature control apparatus for an exhaust gas sensor which is mounted on an exhaust pipe of an internal combustion engine for detecting the concentration of a specific component in an exhaust gas therein, said apparatus comprising:
an electric heater for heating said exhaust gas sensor;
a switching element connected in series to said electric heater for turning on and off the supply of electric power to said electric heater; and
temperature control means for performing on/off control on said switching element so as to maintain the temperature of said exhaust gas sensor at a predetermined value;

said temperature control means comprising:
heating control means for performing heating control on said exhaust gas sensor in accordance with the temperature of said exhaust gas sensor; and
first preheating means and second preheating means for preheating said exhaust gas sensor upon starting of said internal combustion engine;

said heating control means comprising:
resistance value measurement means for measuring a resistance value of said exhaust gas sensor or a resistance value of said electric heater;

temperature determination means for determining based on the resistance value of said exhaust gas sensor or the resistance value of said electric heater whether the temperature of said exhaust gas sensor is in the vicinity of a proper activation temperature thereof; and feedback control means for controlling the on/off state of said switching element in accordance with a correlation characteristic of a target temperature and the resistance value of said exhaust gas sensor or the resistance value of said electric heater with the proper activation temperature of said exhaust gas sensor being made as said target temperature;

wherein said first preheating means includes first energization control means for applying a first voltage to said electric heater in a first period;

said second preheating means includes a second energization control means for applying a second voltage higher than said first voltage to said electric heater in a second period following said first period; and said first and second preheating means operate prior to the operation of said feedback control means.

2. The temperature control apparatus for an exhaust gas sensor as set forth in claim 1, wherein said second preheating means includes a preheating enhancement means for gradually increasing said second voltage with the lapse of time.

3. The temperature control apparatus for an exhaust gas sensor as set forth in claim 1, wherein said temperature control means comprises:
sensor line abnormality detection means for detecting an abnormality in a signal line related to said exhaust gas sensor; and
heating keeping means for keeping heating said exhaust gas sensor in response to said sensor line abnormality detection means;

wherein said sensor line abnormality detection means generates a sensor line abnormality determination signal upon detection of an open-circuit state or a short-circuit state of said signal line for said exhaust gas sensor; and said heating keeping means includes third energization control means for continuously applying a third voltage higher than said first voltage to said electric heater upon generation of said sensor line abnormality determination signal.

4. The temperature control apparatus for an exhaust gas sensor as set forth in claim 1, wherein in order to avoid preheating immediately after starting of said internal combustion engine, said first preheating means includes delayed power supply means that starts operating after a prescribed scavenging period has elapsed from the beginning of the starting of said internal combustion engine.

5. The temperature control apparatus for an exhaust gas sensor as set forth in claim 4, wherein said scavenging period is set to a period which is proportional to a cranking period of said internal combustion engine.

6. The temperature control apparatus for an exhaust gas sensor as set forth in claim 4, wherein said scavenging period is set to a period from the beginning of the starting of the internal combustion engine until the time when a total amount of intake air of said internal combustion engine reaches a predetermined value.

7. The temperature control apparatus for an exhaust gas sensor as set forth in claim 1, wherein said first preheating means includes effective period setting means for setting a prescribed effective period in dependence upon an environmental temperature at the time of the starting of said internal combustion engine, and said first preheating means is made effective over said effective period; and said second preheating means is made effective after said effective period has elapsed.

8. The temperature control apparatus for an exhaust gas sensor as set forth in claim 7, wherein said environmental temperature at the time of the starting of said internal combustion engine is decided depending upon the lower one of the temperature of cooling water of said internal combustion engine and an outside air temperature.

9. The temperature control apparatus for an exhaust gas sensor as set forth in claim 7, wherein said effective period setting means includes maximum preheating time setting means for setting said first period to a prescribed maximum time when said environmental temperature at the time of the starting of said internal combustion engine is not acquired normally.

10. The temperature control apparatus for an exhaust gas sensor as set forth in claim 1, wherein said temperature control means includes preheating completion determination means for determining whether the preheating operation of said second preheating means has been completed; and said exhaust gas sensor comprises:

a gas passageway wall formed of a gas diffusion porous material;

a gas detection chamber defined by an oxygen pump element and an oxygen concentration cell element which are formed of a zirconia solid electrolyte material;

an oxygen concentration reference generation current supply circuit for supplying an oxygen concentration reference generation electric current to said oxygen concentration cell element with one end face of said oxygen concentration cell element being made as an oxygen concentration reference plane; and a pump current control circuit for discharging or supplying oxygen from or to said gas detection chamber so as make the oxygen concentration of said gas detection chamber to be a specified value by controlling a pump current flowing through said oxygen pump element so that an interterminal voltage of said oxygen concentration cell element becomes a specified value;

wherein said exhaust gas sensor functions as a linear sensor for measuring the oxygen concentration of said gas detection chamber by detecting said pump current; and when the interterminal voltage of said oxygen concentration cell element becomes below or equal to a predetermined value, said preheating completion determination means determines the completion of preheating, and makes said heating control means effective.

11. The temperature control apparatus for an exhaust gas sensor as set forth in claim 10, wherein said temperature control means comprises:

preheating abnormality detection means for detecting an abnormality of said second preheating means; and heating keeping control means for keeping heating said exhaust gas sensor in response to said preheating abnormality detection means;

wherein said preheating abnormality detection means generates a preheating abnormality detection signal when the interterminal voltage of said oxygen concentration cell element does not fall below or equal to said predetermined value even if a predetermined time has elapsed after said second preheating means starts preheating; and said heating keeping control means includes a fourth energization control means for continuously applying a fourth voltage higher than said first voltage to said electric heater upon generation of said preheating abnormality detection signal.

12. The temperature control apparatus for an exhaust gas sensor as set forth in claim 10, wherein said temperature control means comprises:

internal resistance value arithmetic calculation means for calculating an internal resistance value of said exhaust gas sensor based on a ratio between a constant high-frequency current that is regularly sampled and supplied to said oxygen concentration cell element and a high-frequency voltage corresponding to said constant high-frequency current; and arithmetic calculation starting determination means for determining the start of arithmetic calculation of said internal resistance value arithmetic calculation means;

wherein said arithmetic calculation starting determination means causes said internal resistance value arithmetic calculation means to start the calculation of said internal resistance value from the point in time at which said preheating completion determination means determines the completion of the preheating of said second preheating means.

13. The temperature control apparatus for an exhaust gas sensor as set forth in claim 10, wherein said temperature control means comprises:

internal resistance value arithmetic calculation means for calculating an internal resistance value of said exhaust gas sensor based on a ratio between a constant high-frequency current that is regularly sampled and supplied to said oxygen concentration cell element and a high-frequency voltage corresponding to said constant high-frequency current; and energization starting command means for commanding the start of supplying of said pump current;

wherein when said exhaust gas sensor has reached an activation starting temperature lower than the proper activation temperature of said exhaust gas sensor, said energization starting command means commands said pump current control circuit to start supplying said pump current to said oxygen pump element.

14. A temperature control apparatus for an exhaust gas sensor which is mounted on an exhaust pipe of an internal combustion engine for detecting the concentration of a specific component in an exhaust gas therein, said apparatus comprising:

an electric heater for heating said exhaust gas sensor;

a switching element connected in series to said electric heater for turning on and off the supply of electric power to said electric heater; and temperature control means for performing on/off control on said switching element so as to maintain the temperature of said exhaust gas sensor at a predetermined value;

said temperature control means comprising;

heating control means for performing heating control on said exhaust gas sensor in accordance with the temperature of said exhaust gas sensor; and preheating means for preheating said exhaust gas sensor upon starting of said internal combustion engine;

said heating control means comprising:
resistance value measurement means for measuring a resistance value of said exhaust gas sensor or a resistance value of said electric heater;
temperature determination means for determining based on the resistance value of said exhaust gas sensor or the resistance value of said electric heater whether the temperature of said exhaust gas sensor is in the vicinity of a proper activation temperature thereof; and
feedback control means for controlling the on/off state of said switching element in accordance with a correlation characteristic of a target temperature and the resistance value of said exhaust gas sensor or the resistance value of said electric heater with the proper activation temperature of said exhaust gas sensor being made as said target temperature;

wherein said preheating means includes a first energization control means for applying a preheating voltage to said electric heater in a prescribed period, and operates prior to the operation of said feedback control means;

said heating control means comprising:
sensor line abnormality detection means for detecting an abnormality of said exhaust gas sensor; and
heating keeping means for keeping heating said exhaust gas sensor in response to said sensor line abnormality detection means;

wherein said sensor line abnormality detection means generates a sensor line abnormality determination signal upon detection of an open-circuit state or a short-circuit state of a signal line for said exhaust gas sensor; and said heating keeping means includes a second energization control means for continuously applying a keeping voltage higher than said preheating voltage to said electric heater upon generation of said sensor line abnormality determination signal.

15. The temperature control apparatus for an exhaust gas sensor as set forth in claim 14, wherein
said first preheating means includes effective period setting means for setting a prescribed effective period in dependence upon an environmental temperature at the time of the starting of said internal combustion engine, and said first preheating means is made effective over said effective period; and
said heating keeping means is made effective after said effective period has elapsed.

16. The temperature control apparatus for an exhaust gas sensor as set forth in claim 14, wherein
said temperature control means comprises:
heater resistance value measurement means for measuring the resistance value of said electric heater;
sensor temperature estimation means for estimating the temperature of said exhaust gas sensor based on the resistance value of said electric heater;
heater abnormality storage means for determining and storing an abnormal state of said electric heater; and
driving stopping means for stopping supplying electric power to said electric heater in response to said heater abnormality storage means;

wherein when an electric current supplied upon said switching element for supplying electric power to said electric heater being driven into a conductive state exceeds a predetermined value, said heater abnormality storage means determines and stores a short-circuit abnormality state in which said electric heater or a power supply circuit for said electric heater is short-circuited;

when an electric current supplied to an open-circuit detection resistor connected in parallel to said switching element is less than or equal to a predetermined value upon said switching element for supplying electric power to said electric heater being interrupted, said heater abnormality storage means determines and stores an open-circuit abnormality state in which said electric heater or said power supply circuit is open-circuited; and when said heater abnormality storage means stores at least said short-circuit abnormality state, said driving stopping means stops supplying electric power to said electric heater.

17. The temperature control apparatus for an exhaust gas sensor as set forth in claim 14, wherein said temperature control means includes a microprocessor for controlling an on/off ratio of said switching element, and said microprocessor has a fuel injection control function for controlling fuel injection to said internal combustion engine.

* * * * *